(12) United States Patent
Shimomura et al.

(10) Patent No.: US 8,110,688 B2
(45) Date of Patent: Feb. 7, 2012

(54) METHOD FOR PRODUCING INDOLE DERIVATIVE HAVING PIPERIDINE RING

(75) Inventors: Naoyuki Shimomura, Tsukuba (JP); Atsushi Kamada, Tsukuba (JP); Mamoru Miyazawa, Kamisu (JP); Koichi Ito, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 1124 days.

(21) Appl. No.: 11/914,115

(22) PCT Filed: Nov. 5, 2006

(86) PCT No.: PCT/JP2006/309461
§ 371 (c)(1),
(2), (4) Date: Nov. 9, 2007

(87) PCT Pub. No.: WO2006/121106
PCT Pub. Date: Nov. 16, 2006

(65) Prior Publication Data
US 2010/0197926 A1 Aug. 5, 2010

(30) Foreign Application Priority Data

May 11, 2005 (WO) .................. PCT/JP2005/008632
Nov. 10, 2005 (JP) ................. 2005-325713

(51) Int. Cl.
*C07D 405/14* (2006.01)
*C07D 311/22* (2006.01)
(52) U.S. Cl. ........................................ 546/201; 549/401
(58) Field of Classification Search .................. 546/201; 549/401
See application file for complete search history.

(56) References Cited

U.S. PATENT DOCUMENTS

| | | | |
|---|---|---|---|
| 5,545,644 A | 8/1996 | Macor et al. | |
| 5,990,114 A | 11/1999 | Leonardi et al. | |
| 6,071,920 A | 6/2000 | Leonardi et al. | |
| 6,329,366 B1 | 12/2001 | Fairhurst et al. | |
| 6,448,243 B1 | 9/2002 | Kitazawa et al. | |
| 6,844,338 B2 | 1/2005 | Fairhurst et al. | |
| 7,538,123 B2 | 5/2009 | Suzuki et al. | |
| 2002/0019531 A1 | 2/2002 | Kitazawa et al. | |
| 2002/0086999 A1 | 7/2002 | Kitazawa et al. | |
| 2002/0193383 A1 | 12/2002 | Leonardi et al. | |
| 2003/0130287 A1 | 7/2003 | Ackermann et al. | |
| 2003/0225068 A1 | 12/2003 | Fairhurst et al. | |
| 2004/0024023 A1 | 2/2004 | Bernotas et al. | |
| 2004/0147581 A1 | 7/2004 | Taylor et al. | |
| 2005/0033056 A1 | 2/2005 | Wong | |
| 2005/0256103 A1 | 11/2005 | Suzuki et al. | |
| 2007/0219179 A1 | 9/2007 | Suzuki et al. | |
| 2008/0027039 A1 | 1/2008 | Arakawa et al. | |

FOREIGN PATENT DOCUMENTS

| | | |
|---|---|---|
| EP | 714894 A1 | 6/1996 |
| EP | 0 976 732 | 2/2000 |
| JP | 8-225568 A | 9/1996 |
| JP | 2002-114684 A | 4/2002 |
| JP | 2002/114684 A1 | 4/2002 |
| JP | 2002-530405 A | 9/2002 |
| JP | 2002/530405 A | 9/2002 |
| JP | 2003/533523 A | 11/2003 |
| JP | 2003-533523 A | 11/2003 |
| WO | WO-96/05817 A1 | 2/1996 |
| WO | WO-97/31637 A1 | 9/1997 |
| WO | WO-98/43956 A | 10/1998 |
| WO | WO 98/43956 A1 | 10/1998 |
| WO | WO-99/06384 A1 | 2/1999 |
| WO | WO 99/06384 A1 | 2/1999 |
| WO | WO 03/059351 A1 | 7/2003 |
| WO | WO-03/059351 A1 | 7/2003 |
| WO | WO-2004/009548 A1 | 1/2004 |
| WO | WO 2004/009548 A1 | 1/2004 |
| WO | WO-2004/045509 A2 | 6/2004 |
| WO | WO 2004/045509 A2 | 6/2004 |
| WO | WO-2004/082584 A | 9/2004 |
| WO | WO-2006/108389 A1 | 11/2005 |
| WO | WO-2006/082872 A1 | 8/2006 |
| WO | WO-2006/121104 A1 | 11/2006 |
| WO | WO-2006/121106 A1 | 11/2006 |

OTHER PUBLICATIONS

Shimomura et al. "method of producing . . . " CA145:489136 (2006).*
Sakaguchi et al. "Preparation of 5-HT1A . . . " CA145:505336 (2006).*
Bauvois et al. "Synthesis and . . . " J. Med. Chem. 46 p. 3900-3913 (2003).*
Chandler et al. "Structural revision . . . " J. Chem. Soc. Perkin Trans. p. 2271-2284 (1992).*
Office Action issued on Jun. 24, 2009 in copending U.S. Appl. No. 11/795,923.
Anthony R. West, "Solid state chemistry and its applications," Wiley, New York, 1986, pp. 358 and 365.
Lecci et al., J. of Pharmacology and Experimental Therapeutics, vol. 262, No. 1, pp. 181-189 (1992).
Testa et al., J. of Pharmacology and Experimental Therapeutics, vol. 290, No. 3, pp. 1258-1269 (1999). Andersson et al., Drugs, vol. 63, No. 23, pp. 2595-2611 (2003).
Coe et al., Tetrahedron Letters, vol. 37, No. 34, pp. 6045-6048 (1996).
Arai et al., Tetrahedron Letters, vol. 39, No. 1, pp. 71-74 (1998).
Tischler et al., Tetrahedron Letters, vol. 27, No. 15, pp. 1653-1656 (1986).
Sakamoto et al., Chem. Pharm. Bull., vol. 34, pp. 2362-2368 (1986).
Emerson et al., Organic Reactions, vol. 4, pp. 174-255, (1948).
Lane, Clinton F., Synthesis, pp. 135-146 (1975).
Stowell et al., Synthesis, p. 127-128 (1974).
Abdel-Magid et al., J. Org. Chem., vol. 61, No. 11, pp. 3849-3862 (1996).
Matassa et al., J. Med. Chem., vol. 33, No. 9, pp. 2621-2629 (1990).
Green et al., Protective Groups in Organic Chemistry, Second Edition, pp. 248-251 (1991).

(Continued)

*Primary Examiner* — Celia Chang
(74) *Attorney, Agent, or Firm* — Birch, Stewart, Kolasch & Birch, LLP

(57) ABSTRACT

It is possible to commercially advantageously prepare 1-{1-[2-(7-methoxy-2,2-dimethyl-4-oxochroman-8-y)ethyl]piperidin-4-yl}-N-methyl-1H-indole-6-carboxamide by coupling (7-methoxy-2,2-dimethyl-4-oxochroman-8-yl) acetaldehyde, which is obtained by oxidizing 8-(2-hydroxyethyl)-7-methoxy-2,2-dimethylchroman-4-one, with N-methyl-1-(piperidin-4-yl)-1H-indole-6-carboxamide.

8 Claims, No Drawings

OTHER PUBLICATIONS

Rosowsky et al., J. Med. Chem., vol. 34, No. 1, pp. 227-234 (1991).
Brzostowska et al., Heterocycles, vol. 32, No. 10, pp. 1969-1972 (1991).
Romero et al., J. Med. Chem., vol. 37, No. 7, pp. 999-1014 (1994).
Dodd et al., Synthetic Communications, vol. 23, No. 7, pp. 1003-1008 (1993).
Sim et al., Synlett, vol. 10, pp. 827-828 (1994).
Green et al., Protective Groups in Organic Chemistry, Second Edition, pp. 309-405 (1991).
Hirai et al., Tetrahedron Letters, vol. 31, No. 33, pp. 4755-4756 (1990).
Brown et al., Tetrahedron, vol. 35, pp. 567-607 (1979).
Brown et al., Aldrichchimica Acta, vol. 12, No. 1, pp. 3-11 (1979).
Hudlicky et al., Org. React., vol. 35, pp. 513-637 (1988).
Nichols et al., J. Med. Chem., vol. 34, pp. 276-281 (1991).
Sato et al., Chem. Pharm. Bull., vol. 39, No. 7, pp. 1760-1772 (1991).
Chilin et al., J. Org. Chem., vol. 56, No. 3, pp. 980-983 (1991).
Dike et al., Tetrahedron, vol. 47, No. 26, pp. 4775-4786 (1991).
Jagadeesh et al., Synthetic Communications, vol. 31, No. 10, pp. 1547-1557 (2001).
Cannon et al., Chem., vol. 27, No. 7, pp. 2093-2095 (1990).
Lai et al., Tetrahedron Letters, vol. 34, No. 43, pp. 6849-6852 (1993).
Masquelin et al., Synthesis, pp. 780-786 (1995).
Banfield et al., Org. Lett. vol. 3, No. 21, pp. 3325-3327 (2001).
Green et al., Protecting Groups in Organic Chemistry, Second Edition, pp. 118-142 (1991).
Gibson et al., J. Chem. Soc., vol. 4, pp. 447-455 (1997).
Peroutka, S., Ann. Rev. Neurosci., vol. 11, pp. 45-60, (1988).
Neurotransmitter Today, vol. 19, No. 2, pp. 131-146, (1997).
Farde et al., Neuropsychopharmacology, vol. 22, No. 4, pp. 422-429, (2000).
Barros et al., European J. of Pharmacology, vol. 482, pp. 197-203, (2003).
Harder et al., Neuropharmacology, vol. 39, pp. 547-552, (2000).
Harder et al., Psychopharmacology, vol. 127, pp. 245-254, (1996).
Yasuno et al., Am. J. Psychiatry, vol. 160, No. 2, pp. 1-7, (2003).
Lecci et al., J. of Pharm. and Exp. Therapeutics, vol. 262, No. 1, pp. 181-189, (1992).
Testa et al., J. of Pharm. and Exp. Therapeutics, vol. 290, No. 3, pp. 1258-1269 (1999).
Andersson et al., Drugs, vol. 63, No. 23, pp. 2595-2611, (2003).
Bourin et al., Biomed & Pharmacother, vol. 50, pp. 7-12, (1996).
Hansenne et al., Psych. Medicine, vol. 32, pp. 935-941, (2002).
Wilson et al., Am. J. Phys. Med. Rehabil., vol. 81, No. 5, pp. 364-372, (2002).
Fletcher et al., TiPS, vol. 14, pp. 441-448, (1993).
Zhou et al., Alcohol. Clin. and Exp. Research, vol. 22, No. 1, pp. 266-269, (1998).
Carey et al., Behavioural Brain Research, vol. 132, pp. 37-46, (2002).
Boers et al., Cephalalgia, vol. 24, pp. 99-109, (2004).
Balducci et al., Psychopharmacology, vol. 167, pp. 28-36, (2003).
Gupta et al., Indian J. Physiol. Pharmacol., vol. 46, No. 4, pp. 463-467, (2002).
Dabire, H., Therapie, vol. 46, pp. 421-429, (1991).
Kruger et al., vol. 10, No. 12, pp. 2651-2656, (1999).
Suchanek et al., Euro. J. of Pharmacology, vol. 355, pp. 95-101, (1998).
Bibbiani et al., Neurology, vol. 57, pp. 1829-1834, (2001).
Rasmussen et al., J. of Pharmacology and Exp. Therapeutics, vol. 294, No. 2, pp. 688-700, (2000).
Gu et al., J. of Pharmacology and Exp. Therapeutics, vol. 310, No. 3, pp. 1266-1272, (2004).
Thor et al., Brain Research, vol. 946, pp. 290-297, (2002).
Office Action issued on Apr. 7, 2011 in copending U.S. Appl. No. 11/913,931.
J. Dean, Analytical Chemistry Handbook, Section 10, pp. 10.24-10.26, McGraw-Hill, Inc. 1995.
Kirk-Othmer, "Crystallization," Encyclopedia of Chemical Technology, vol. 8, p. 95-147, John Wiley & Sons, Inc. 2002.
S. Byrn et al., Solid-State Chemistry of Drugs, 2nd Edition. p. 63, SSCI, Inc. 1999.
S.M. Berge et al., "Pharmaceutical Salts," Journal of Pharmaceutical Sciences, vol. 66, No. 1, p. 1-19, 1977.
Japanese Office Action for Japanese Application No. 2007-528313, dated Dec. 9, 2011.

* cited by examiner

METHOD FOR PRODUCING INDOLE DERIVATIVE HAVING PIPERIDINE RING

This Nonprovisional application claims priority under 35 U.S.C. §120 on PCT/JP2006/309461 filed on May 11, 2006, claims priority under 119(e) on U.S. Provisional Application Ser. No. 11/126,209 filed on May 11, 2005, and claims priority under 35 U.S.C. §119(a) on Patent Application No. 2005-325713 filed in Japan on Nov. 10, 2005 and PCT Application No. PCT/W2005/008632 filed in Japan on May 11, 2005; the entire contents of which are hereby incorporated by reference.

TECHNICAL FIELD

The present invention relates to a method for producing 1-{1-[2-(7-methoxy-2,2-dimethyl-4-oxochroman-8-yl)ethyl]piperidin-4-yl}-N-methyl-1H-indole-6-carboxamide which has antagonistic activity and binding activity to $5HT_{1A}$ and is useful as a preventive agent or a therapeutic agent for lower urinary tract symptom, in particular urine storage symptom.

BACKGROUND ART

There is known $5HT_{1A}$ receptor as one of serotonin receptors, and compounds having antagonistic activity and binding affinity to $5HT_{1A}$ are expected as preventive or therapeutic agents for depression, anxiety disorder, cognitive impairment, urinary disturbance, etc. Various compounds having a piperidine ring have been already reported as such compounds (see Patent Document 1, Patent Document 2 and Patent Document 3).

[Patent Document 1] WO99/06384
[Patent Document 2] JP-A-2002-114684
[Patent Document 3] WO98/43956

DISCLOSURE OF THE INVENTION

The present inventors found, as novel piperidine-ring-containing indole derivatives having antagonistic activity and binding affinity to $5HT_{1A}$, compounds represented by the following general formula (I)

[Formula 1]

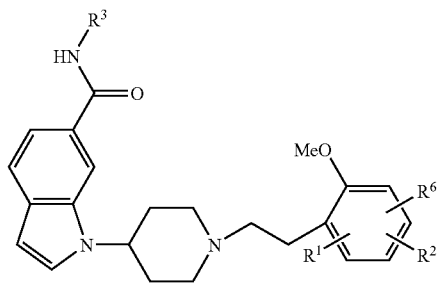

(I)

wherein $R^1$ and $R^2$ are substituents adjacent to each other, and together with two carbon atoms to which they are respectively attached, form:
(1) a 5- to 7-membered non-aromatic carbocyclic group,
(2) a 5- to 7-membered non-aromatic heterocyclic group,
(3) a 6-membered aromatic carbocyclic group, or
(4) a 5- or 6-membered aromatic heterocyclic group,
which may be substituted by 1 to 4 substituents selected from the following substituent group B1;
$R^3$ represents a hydrogen atom or a methyl group; and
$R^6$ represents a substituent selected from the following substituent group A1, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group, which may be substituted by 1 to 3 substituents selected from the group consisting of a halogen atom, a hydroxyl group, and a C1-C6 alkoxy group, (14) a C1-C6 alkoxy group, which may be substituted by 1 to 3 halogen atoms, (15) an amino group, which may be substituted by a substituent selected from the group consisting of a C1-C6 alkyl group, a formyl group, a C1-C6 alkanoyl group, and a C1-C6 alkylsulfonyl group, and (16) a carbamoyl group, which may be substituted by one or two C1-C6 alkyl groups;

Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group, which may be substituted by a halogen atom, a hydroxyl group, and a C1-C6 alkoxy group, (15) a C1-C6 alkoxy group, which may be substituted by 1 to 3 halogen atoms, (16) an amino group, which may be substituted by a substituent selected from the group consisting of a C1-C6 alkyl group, a formyl group, a C1-C6 alkanoyl group, and a C1-C6 alkylsulfonyl group, (17) a carbamoyl group, may be substituted by one or two C1-C6 alkyl groups, (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl groups attaching to the same carbon atom, together with an oxygen atom and the carbon atom, and already filed patent applications (International Patent Application No. PCT/JP2005/008632 and U.S. patent application Ser. No. 11/126,209). These compounds exhibit antagonistic activity and binding affinity to $5HT_{1A}$ and are useful as a preventive agent or a therapeutic agent for lower urinary tract symptom, in particular urine storage symptom.

Particularly, 1-{1-[2-(7-methoxy-2,2-dimethyl-4-oxochroman-8-yl)ethyl]piperidin-4-yl}-N-methyl-1H-indole-6-carboxamide, the compound included in the above general formula (I) and represented by the following formula (i)

[Formula 2]

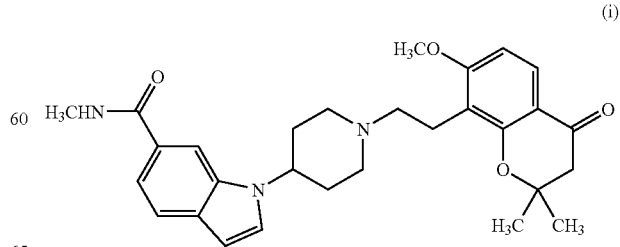

(i)

is expected to have an excellent effect.

Accordingly, an object of the present invention is to provide a method for producing the compound (I) and intermediate compounds therefor.

The present inventors have conducted intensive studies and consequently have found a method for producing the compound (I) and completed the present invention.

That is, the present invention relates to the following.

(1) A production method of 1-{1-[2-(7-methoxy-2,2-dimethyl-4-oxochroman-8-yl)ethyl]piperidin-4-yl}-N-methyl-1H-indole-6-carboxamide represented by the following formula (i):

[Formula 6]

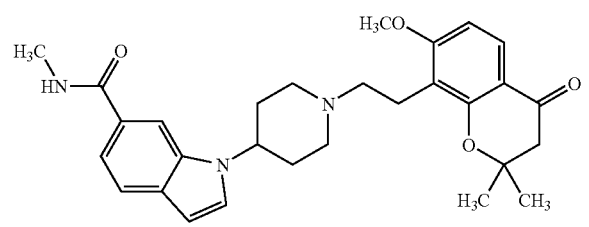

comprising coupling (7-methoxy-2,2-dimethyl-4-oxochroman-8-yl)acetaldehyde represented by the following formula (a):

[Formula 4]

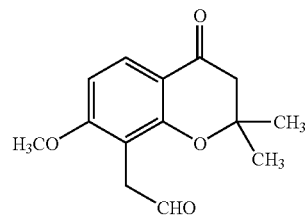

which is obtained by oxidizing 8-(2-hydroxyethyl)-7-methoxy-2,2-dimethylchroman-4-one represented by the following formula (a-6):

[Formula 3]

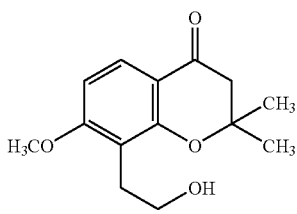

with N-methyl-1-(piperidin-4-yl)-1H-indole-6-carboxamide represented by the following formula (b):

[Formula 5]

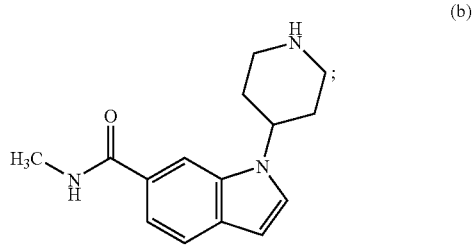

(2) The production method according to the above (1) wherein 8-(2-hydroxyethyl)-7-methoxy-2,2-dimethylchroman-4-one represented by the following formula (a-6):

[Formula 7]

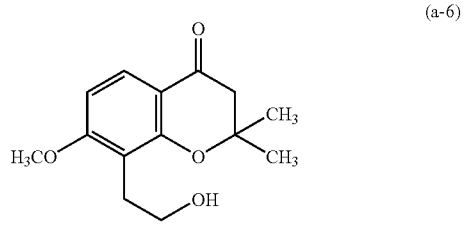

is obtained by removing a protecting group of the compound represented by the following formula (a-5):

[Formula 8]

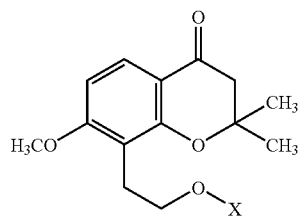

wherein X represents a protecting group of the hydroxyl group;

(3) The production method according to the above (1) or (2) wherein 8-(2-hydroxyethyl)-7-methoxy-2,2-dimethylchroman-4-one represented by the following formula (a-6):

[Formula 9]

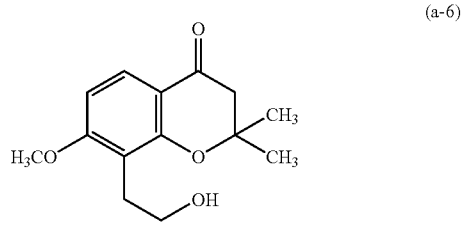

is obtained by reacting the compound represented by the following formula (a-4):

[Formula 10]

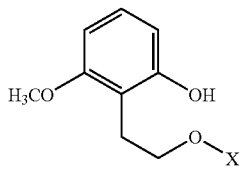

(a-4)

wherein X represents a protecting group of the hydroxyl group, with methylcrotonic acid to obtain a compound represented by the following formula (a-5):

[Formula 11]

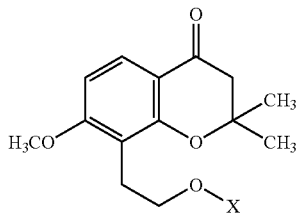

(a-5)

wherein X means the same as defined above, and removing the protecting group of the compound (a-5);

(4) The production method according to any of the above (1) to (3) wherein 8-(2-hydroxyethyl)-7-methoxy-2,2-dimethylchroman-4-one represented by the following formula (a-6):

[Formula 12]

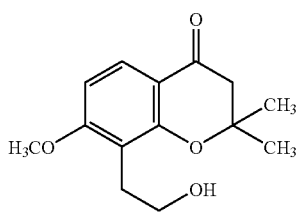

(a-6)

is obtained by reacting the compound represented by the following formula (a-3):

[Formula 13]

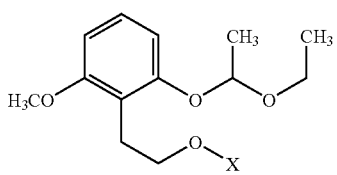

(a-3)

wherein X represents a protecting group of the hydroxyl group, with an acid to obtain a compound represented by the following formula (a-4):

[Formula 14]

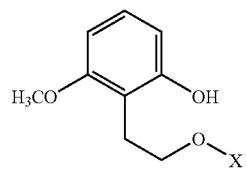

(a-4)

wherein X means the same as defined above, and reacting the compound (a-4) with methylcrotonic acid to obtain a compound represented by the following formula (a-5):

[Formula 15]

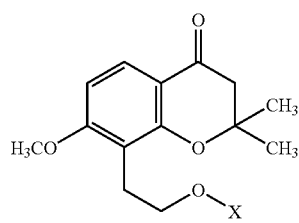

(a-5)

wherein X means the same as defined above, and removing the protecting group of the compound (a-5);

(5) The production method according to any of the above (1) to (4) wherein 8-(2-hydroxyethyl)-7-methoxy-2,2-dimethylchroman-4-one represented by the following formula (a-6):

[Formula 16]

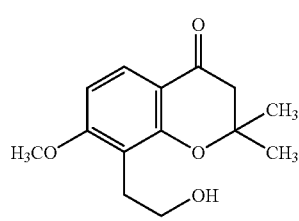

(a-6)

is obtained by protecting a hydroxyl group of 2-[2-(1-ethoxyethoxy)-6-methoxyphenyl]ethanol represented by the following formula (a-2):

[Formula 17]

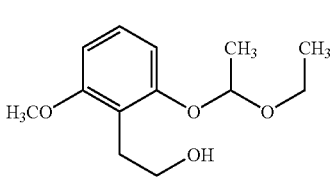

(a-2)

to obtain a compound represented by the following formula (a-3):

[Formula 18]

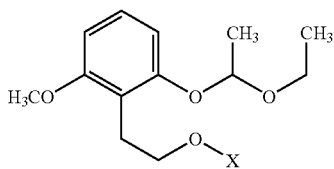
(a-3)

wherein X represents a protecting group of the hydroxyl group, reacting the compound (a-3) with an acid to obtain a compound represented by the following formula (a-4):

[Formula 19]

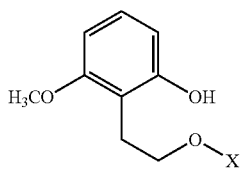
(a-4)

wherein X means the same as defined above, and reacting the compound (a-4) with methylcrotonic acid to obtain a compound represented by the following formula (a-5):

[Formula 20]

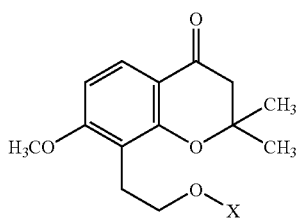
(a-5)

wherein X means the same as defined above, and removing the protecting group of the compound (a-5);

(6) The production method according to any of the above (1) to (5) wherein 8-(2-hydroxyethyl)-7-methoxy-2,2-dimethylchroman-4-one represented by the following formula (a-6):

[Formula 21]

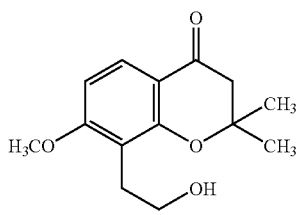
(a-6)

is obtained by reducing ethyl [2-(1-ethoxyethoxy)-6-methoxyphenyl]acetate represented by the following formula (a-1):

[Formula 22]

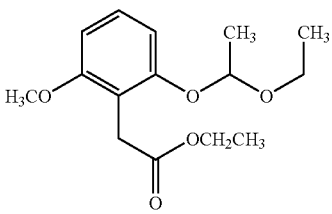
(a-1)

to obtain 2-[2-(1-ethoxyethoxy)-6-methoxyphenyl]ethanol represented by the following formula (a-2):

[Formula 23]

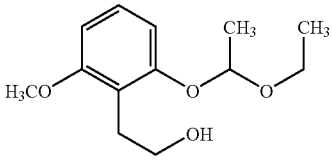
(a-2)

protecting a hydroxyl group of the compound to obtain a compound represented by the following formula (a-3):

[Formula 24]

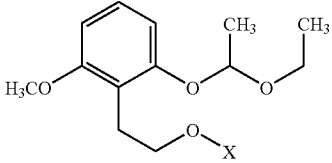
(a-3)

wherein X represents a protecting group of the hydroxyl group, reacting the compound (a-3) with an acid to obtain a compound represented by the following formula (a-4):

[Formula 25]

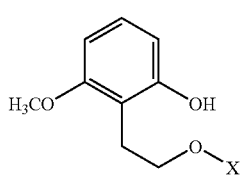
(a-4)

wherein X means the same as defined above, and reacting the compound (a-4) with methylcrotonic acid to obtain a compound represented by the following formula (a-5):

[Formula 26]

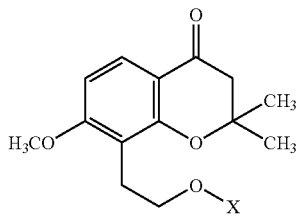
(a-5)

wherein X means the same as defined above, and removing the protecting group of the compound (a-5);

(7) The production method according to any of the above (1) to (6) wherein 8-(2-hydroxyethyl)-7-methoxy-2,2-dimethylchroman-4-one represented by the following formula (a-6):

[Formula 27]

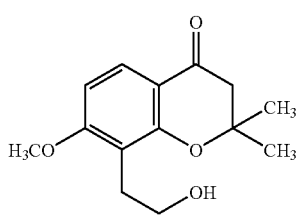
(a-6)

is obtained by reacting 1-(1-ethoxyethoxy)-3-methoxybenzene represented by the following formula:

[Formula 28]

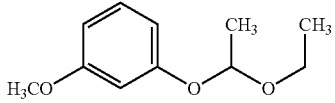

with ethyl bromoacetate to obtain ethyl [2-(1-ethoxyethoxy)-6-methoxyphenyl]acetate represented by the following formula (a-1):

[Formula 29]

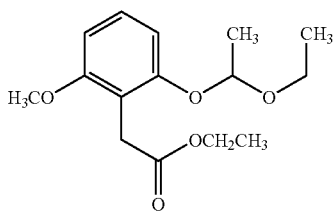
(a-1)

and reducing the compound (a-1) to obtain 2-[2-(1-ethoxyethoxy)-6-methoxyphenyl]ethanol represented by the following formula (a-2):

[Formula 30]

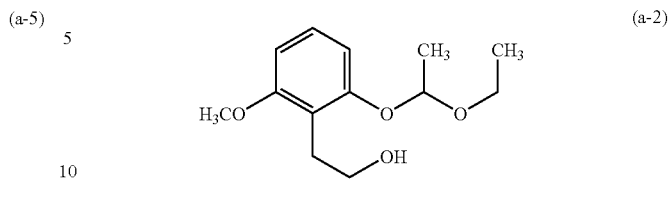
(a-2)

protecting a hydroxyl group of the compound (a-2) to obtain a compound represented by the following formula (a-3):

[Formula 31]

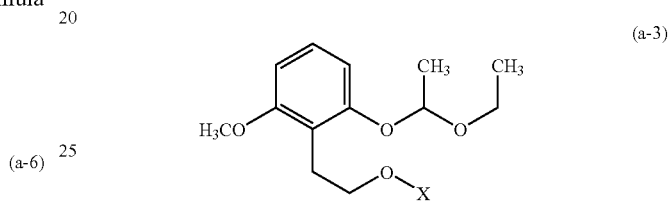
(a-3)

wherein X represents a protecting group of the hydroxyl group, reacting the compound (a-3) with an acid to obtain a compound represented by the following formula (a-4):

[Formula 32]

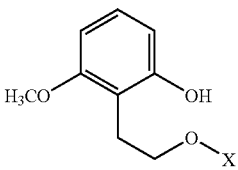
(a-4)

wherein X means the same as defined above, and reacting the compound (a-4) with methylcrotonic acid to obtain a compound represented by the following formula (a-5):

[Formula 33]

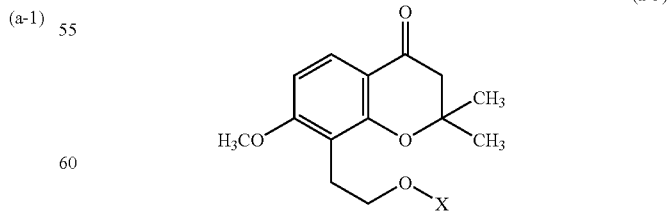
(a-5)

wherein X means the same as defined above, and removing the protecting group of the compound (a-5);

(8) The production method according to any of the above (2) to (7) wherein X is a benzoyl group;

(9) A compound represented by the following formula (II)

[Formula 34]

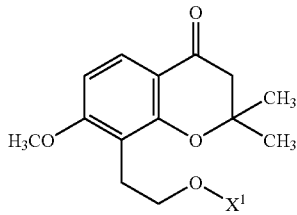

(II)

wherein $X^1$ represents a hydrogen atom or a protecting group of the hydroxyl group;

(10) The compound according to the above (9) wherein the protecting group of the hydroxyl group is a benzoyl group;

(11) 2-(7-methoxy-2,2-dimethyl-4-oxochroman-8-yl)ethyl benzoate or 8-(2-hydroxyethyl)-7-methoxy-2,2-dimethyl-chroman-4-one;

(12) A production method of 1-{1-[2-(7-methoxy-2,2-dimethyl-4-oxochroman-8-yl)ethyl]piperidin-4-yl}-N-methyl-1H-indole-6-carboxamide represented by the following formula (i):

[Formula 36]

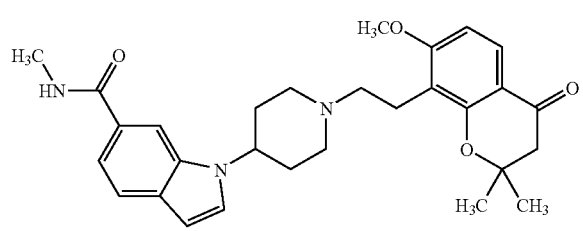

(i)

comprising reacting a compound represented by the following formula (c-3):

[Formula 35]

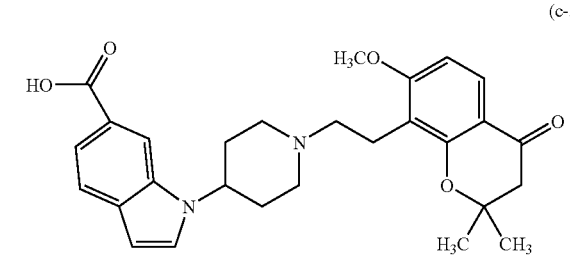

(c-3)

and methylamine;

(13) The production method according to the above (12) wherein the compound represented by the following formula (c-3):

[Formula 37]

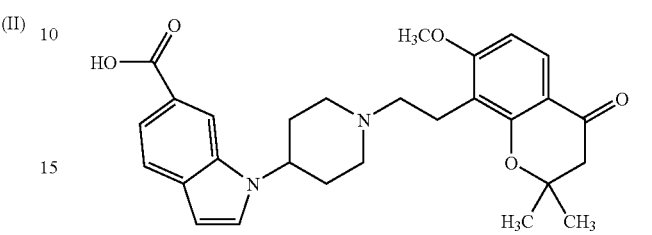

(c-3)

is obtained by hydrolyzing a compound represented by the following formula (c-2):

[Formula 38]

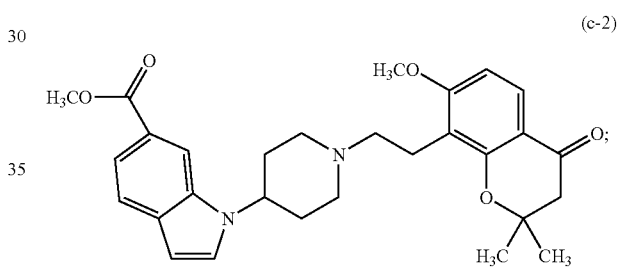

(c-2)

(14) The production method according to the above (12) wherein the compound represented by the following formula (c-3):

[Formula 39]

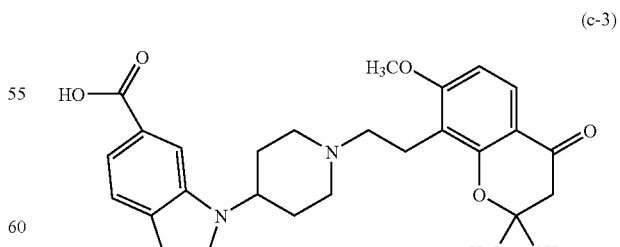

(c-3)

is obtained by reacting a compound represented by the following formula (a):

[Formula 40]

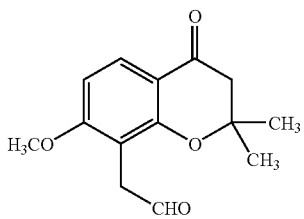

(a)

and a compound represented by the following formula (c-1):

[Formula 41]

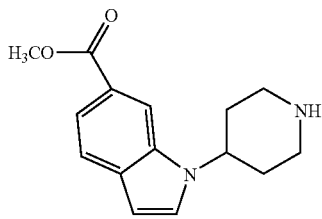

(c-1)

or a salt thereof to obtain a compound represented by the following formula (c-2):

[Formula 42]

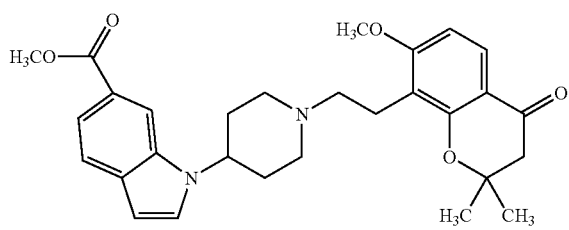

(c-2)

and hydrolyzing the compound;

(15) The production method according to the above (12) wherein the compound represented by the following formula (c-3):

[Formula 43]

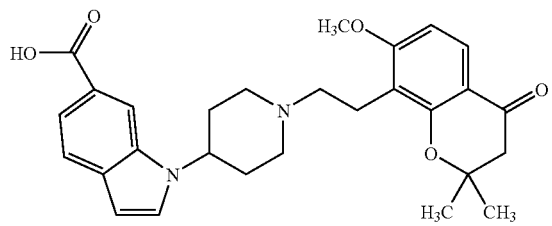

(c-3)

is obtained by reacting a compound represented by the following formula (a):

[Formula 44]

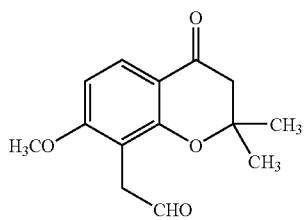

(a)

and a compound represented by the following formula (c-1):

[Formula 46]

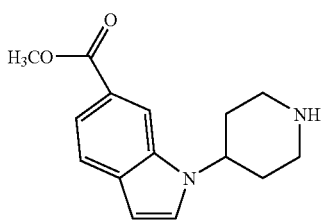

(c-1)

which is obtained by removing protecting group of a compound represented by the following formula (b'-4):

[Formula 45]

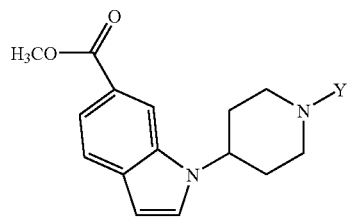

(b'-4)

wherein Y represents a protecting group of a secondary amine, or a salt thereof to obtain a compound represented by the following formula (c-2):

[Formula 47]

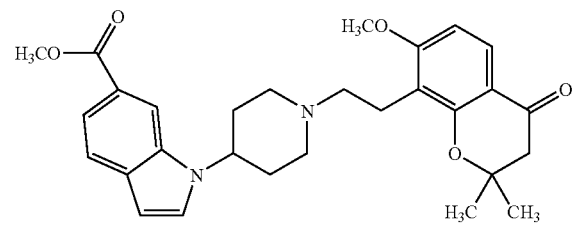

(c-2)

and hydrolyzing the compound (c-2); and

(16) The production method according to the above (15) wherein Y is benzyloxycarbonyl.

According to the present invention, 1-{1-[2-(7-methoxy-2,2-dimethyl-4-oxochroman-8-yl)ethyl]piperidin-4-yl}-N-methyl-1H-indole-6-carboxamide can be prepared industrially advantageously. In addition, production intermediates which can be used advantageously for such production is provided by the present invention.

BEST MODE FOR CARRYING OUT THE INVENTION

The method for producing the compound represented by the following formula (i) of the present invention is shown below.

Step (1)

Step (1) is a step of subjecting a compound represented by the following formula (a) and a compound represented by the following formula (b) to a coupling reaction and thereby obtaining a compound represented by the following formula (i).

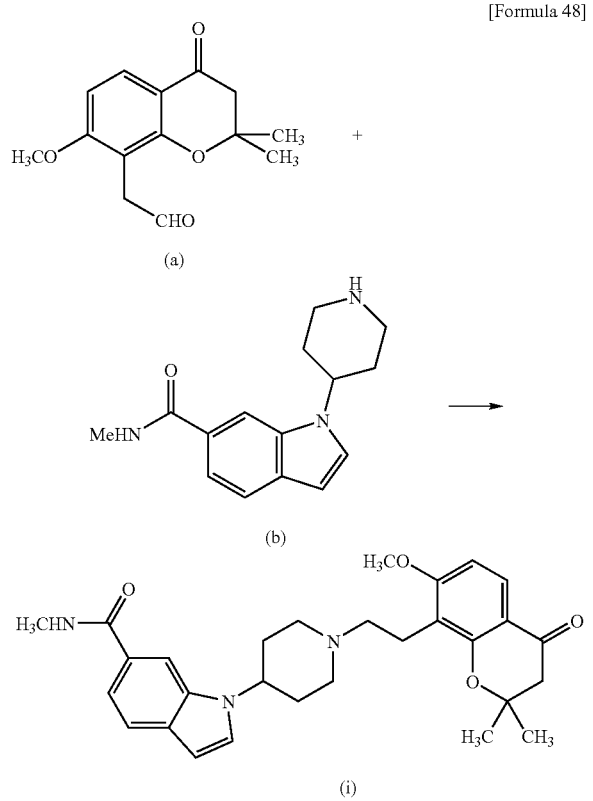

[Formula 48]

The coupling reaction in Step (1) can be preferably performed under reductive amination reaction conditions, that is, similar conditions as ordinarily used for reductive amination reaction of a carbonyl compound and an amine compound. The reduction reaction of this step is not particularly limited and includes, for example, reductive amination reaction with a reducing agent such as borane and borohydride complex compounds and catalytic reduction reaction under a hydrogen atmosphere using a metal catalyst.

Examples of the reductive amination reaction using a borohydride complex compound include, for example, methods described in W. S. Emerson, Organic Reactions, 4. 174 (1948), C. F. Lane, Synthesis, 135 (1975); J. C. Ctowell and S. J. Pedegimas, Synthesis, 127 (1974) and A. F. Abdel-Magid, K. G. Carson, B. D. Harris, C. A. Marryanoff and R. D. Shah, Journal of Organic Chemistry, 61, 3849 (1996), etc. As a borohydride complex compound, for example, sodium borohydride, sodium cyanoborohydride, sodium triacetoxyborohydride can be used. When a borohydride complex compound is used as a reducing agent, the solvent is not particularly limited as long as it does not inhibit the reaction and dissolves the starting substances to some extent, but specific examples thereof include methanol, ethanol, tetrahydrofuran, N,N-dimethylformamide, methylene chloride, 1,2-dichloroethane.

The compound (b) is used at a ratio of 0.8 to 2.5 equivalents, preferably 1 to 1.5 equivalents, with respect to compound (a). The borohydride complex compound is used at a ratio of 1 to 3 equivalents, preferably 1 to 1.5 equivalents, with respect to compound (a). The reaction time is not particularly limited but it is ordinarily between 0.5 and 48 hours, preferably between 0.5 and 12 hours. The reaction temperature is not particularly limited but it is ordinarily between −78° C. and a reflux temperature of the solvent, and preferably between a temperature on ice and room temperature.

When a catalytic reduction reaction is carried out under a hydrogen atmosphere, the solvent used is not particularly limited, as long as it does not inhibit the reaction and examples of the solvent include methanol, ethanol, tetrahydrofuran and 1,4-dioxane. Examples of the metal catalyst used for the reaction include palladium, platinum oxide and Raney nickel. The reaction time is not particularly limited but it is ordinarily between 1 and 48 hours, preferably between 1 and 24 hours. The reaction conditions are not particularly limited and the reaction can be carried out at a temperature between room temperature and a reflux temperature of the solvent at a pressure between an ordinary pressure and 15 MPa, preferably between room temperature and 60° C. at a pressure between an ordinary pressure and 0.5 MPa.

The compound (a) can be obtained through the following Steps (A-1) to (A-6) and Step (A).

Step (A-1)

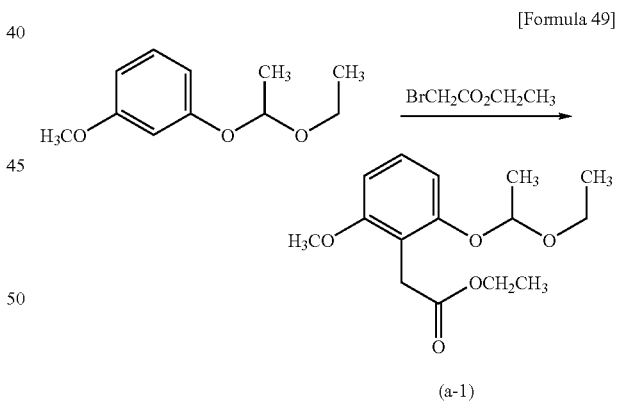

[Formula 49]

Step (A-1) is a step of obtaining a compound represented by formula (a-1) by reacting 1-(1-ethoxyethoxy)-3-methoxybenzene and ethyl bromoacetate.

This step can be performed in the presence of a strong base such as n-butyllithium, if necessary. The reaction solvent is not particularly limited as long as it does not inhibit the reaction and dissolves the starting substances to some extent and specific examples include tetrahydrofuran, heptane, hexane, toluene, 1,2-dimethoxyethane, diethyl ether, 1,2-dichloroethane. The reaction temperature is not particularly limited but it is ordinarily between −78° C. and a reflux temperature of the solvent, and preferably between −78° C. and 0° C. The Step (A-2)

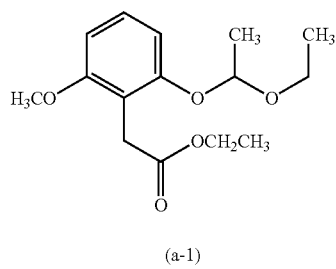

(a-1)

Reduction

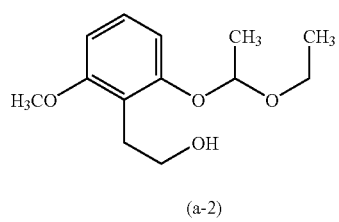

(a-2)

Step (A-2) is a step of obtaining a compound represented by the above formula (a-2) by reducing a compound represented by the above formula (a-1).

The reduction reaction of the ester in Step (A-2) can be carried out under the same conditions as, or according to commonly used conditions in reduction reaction described in, for example, Jikken Kagaku Koza (fourth edition), Vol. 26, pp. 159-266. Examples of the reducing agent used in the reaction include lithium aluminum hydride, lithium borohydride, diisobutyl aluminum hydride, and sodium bis(2-methoxyethoxy)aluminum hydride. The solvent used in the reaction is not particularly limited, as long as it does not inhibit the reaction and dissolves a starting substance to some extent. Preferred examples of such a solvent include ether type solvents such as tetrahydrofuran, diethyl ether, dimethoxyethane, cyclopentyl methyl ether, aromatic hydrocarbon solvents such as toluene and xylene, and methylene chloride. The reaction temperature is not particularly limited. It is ordinarily between −78° C. and a reflux temperature of the solvent, and preferably between −78° C. and room temperature. The reducing agent is used at a ratio between 1 and 3 equivalents, preferably between 1 and 1.5 equivalents, with respect to compound (a-1).

Step (A-3)

[Formula 51]

H₃CO — (a-2) structure with OH — Introduction of a protecting group →

(a-2)

-continued (a-3) structure wherein X represents a protecting group of a hydroxyl group.

Step (A-3) is a step of obtaining a compound represented by the above formula (a-3) by protecting the hydroxyl group of a compound represented by the above formula (a-2).

Examples of protecting group of a hydroxyl group represented by X include protecting groups commonly known protecting groups of a hydroxyl group such as an acetyl group or a benzoyl group but preferably it is a benzoyl group. In this step, when the hydroxyl group is protected by a benzoyl group for example, benzoyl chloride is allowed to react in the presence of a base such as triethylamine in an aromatic hydrocarbon solvent such as toluene and xylene, an ester solvent such as ethyl acetate or an ether solvent such as dimethoxyethane and cyclopentyl methyl ether, so as to obtain a target product. Benzoyl chloride can be used at a ratio between one equivalent and a large excess amount with respect to compound (a-2). There may be cases where preferred results such as the improvement of yield or the reduction of the reaction time are obtained by the coexistence of N,N,N',N'-tetramethylethylenediamine, diisopropylethylamine, N,N-dimethylaniline, or the like, in this reaction. The reaction temperature is between 0 and 100° C., and preferably it is between 0° C. and room temperature. The reaction time is not limited in particular but ordinarily between 0.5 and 48 hours, and preferably it is between 0.5 and four hours.

Step (A-4)

[Formula 52]

(a-3) structure — Acid →

(a-4) structure wherein X means the same as defined above.

Step (A-4) is a step of obtaining a compound represented by the above formula (a-4) by reacting a compound represented by the above formula (a-3) with an acid.

The acid used in this step may be any acid ordinarily used but preferably it is hydrochloric acid. The acid is used in an amount between one equivalent and a large excess amount with respect to compound (a-3). The reaction solvent is not limited in particular as long as it does not inhibit the reaction and dissolves the starting substances to some extent but specific examples thereof include toluene, dimethoxyethane, tetrahydrofuran, water and mixed solvents of these. The reaction temperature is between 0 and 100° C., preferably between 0° C. and room temperature. The reaction time is ordinarily between 0.5 and 48 hours, preferably between 1 and 4 hours.
Step (A-5)

[Formula 53]

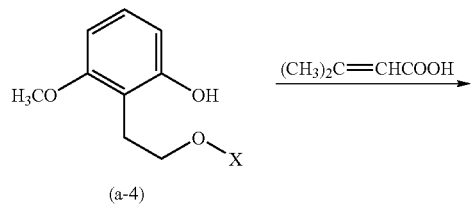

wherein X means the same as defined above.

Step (A-5) is a step of obtaining a compound represented by the above formula (a-5) by reacting a compound represented by the above formula (a-4) and methylcrotonic acid.

This step can be carried out under the similar conditions as those described in publications such as T. Timar et al., "Synthesis of 2,2-Dimethyl-4-Chromanones", J. Heterocyclic Chem., 37, 1389 (2000), J. C. Jaszberenyi et al., "On the Synthesis of Substituted 2,2-Dimethyl-4-Chromanones and Related Compounds" Tetrahedron Letters, 33 (20), 2791-2794, (1992), J. C. Jaszberenyi et al., Heterocycles, 38 (9), 2099, (1994). Other than these methods, compound (a-5) can also be obtained by allowing compound (a-4) to react with methylcrotonic acid in the presence of methanesulfonic acid. Methylcrotonic acid is used at a ratio between one equivalent and a large excess amount with respect to compound (a-4). If necessary, a dehydrating agent such as phosphorus pentoxide may be added in this reaction. The reaction solvent is not limited in particular as long as it does not inhibit the reaction and dissolves the starting substances to some extent but specific examples thereof include methanesulfonic acid. The reaction temperature is between room temperature and 100° C., preferably between 40° C. and 60° C. The reaction time is not limited in particular, but is ordinarily between 0.5 and 48 hours, preferably between 1 and 4 hours.
Step (A-6)

[Formula 54]

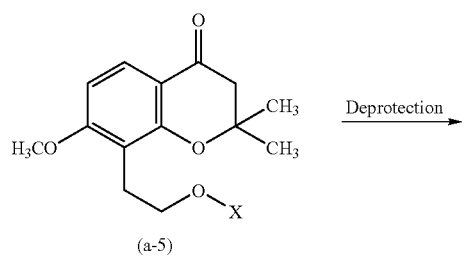

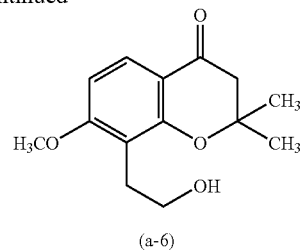

wherein X means the same as defined above.

Step (A-6) is a step of obtaining a compound represented by the above formula (a-6) by deprotection the protecting group of the hydroxyl group of a compound represented by the above formula (a-5).

The reaction can be carried out under similar conditions as those commonly used for deprotection of a protecting group for an alcoholic hydroxyl group described in publications such as T. W. Greene and P. G. M. Wuts, "Protective groups in Organic Synthesis, Second Edition", John Wiley & Sons, Inc. For example, an alcoholic hydroxyl group protected by a benzoyl group or the like is allowed to react with aqueous sodium hydroxide or the like in an organic solvent such as tetrahydrofuran, methanol and ethanol, or in a mixed solvent thereof so as to obtain a product of interest. Sodium hydroxide is used at a ratio between one equivalent and a large excess amount with respect to compound (a-5). The reaction temperature is between 0 and 100° C., preferably between room temperature and 50° C. The reaction time is not limited in particular, but is ordinarily between 0.5 and 48 hours, preferably between 1 and 5 hours.
Step (A)

[Formula 55]

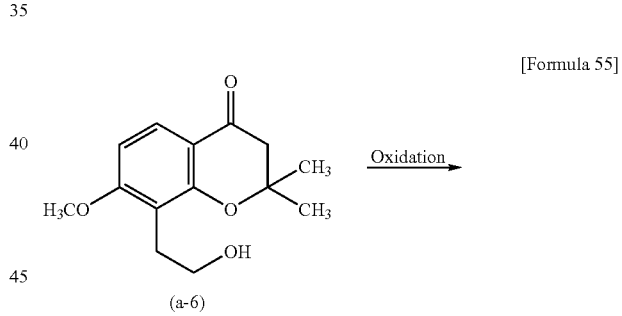

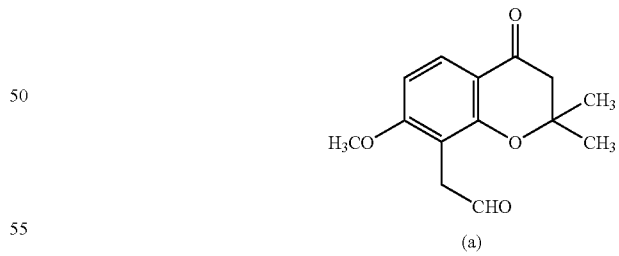

Step (A) is a step of obtaining a compound represented by the above formula (a) by oxidizing a compound represented by the above formula (a-6).

An aldehyde compound can be obtained from an alcohol compound according to a method known to those skilled in the art. Examples of the conventionally known oxidation methods include Swern oxidation, Corey-Kim oxidation, Moffatt oxidation, PCC oxidation, PDC oxidation, Dess-Martin oxidation, SO$_3$-pyridine oxidation and TEMPO oxidation. The reaction solvent is not particularly limited, as long as it does not inhibit the reaction and dissolves a starting substances to some extent and examples thereof include dimethyl sulfoxide, tetrahydrofuran, toluene, methylene chloride, chloroform, ethyl acetate, water, and a mixed solvent thereof. The oxidizing agent is used at a ratio between a catalytic amount and a large excess amount with respect to compound (a-6). The reaction temperature is not limited in particular but it is ordinarily between −78° C. and the reflux temperature of the solvent, preferably between −5° C. and room temperature. The reaction time is not limited in particular, but is ordinarily between 1 and 10 hours, preferably between 1 and 5 hours. In the case of TEMPO oxidation for example, it can be carried out according to the method described in Jikken Kagaku Koza (fourth edition) Vol. 23, Yuki Gosei V, Sanka Hanno, Maruzen Co., Ltd., pp. 369-403. The reaction solvent is not limited in particular as long as it does not inhibit the reaction and dissolves the starting substances to some extent and examples thereof include dimethyl sulfoxide, tetrahydrofuran, toluene, methylene chloride, chloroform, ethyl acetate, water and a mixed solvent thereof. An oxidizing agent, for example, sodium hypochlorite mixed in an aqueous sodium bicarbonate solution, is used at a ratio not less than one equivalent with respect to compound (a-6) in the presence of 2,2,6,6-tetramethylpiperidine oxide-sodium bromide. The reaction temperature is not limited in particular but it is ordinarily between −20° C. and room temperature, preferably between −5° C. and room temperature. The reaction time is not limited in particular but it is ordinarily between 1 and 10 hours, preferably between 1 and 5 hours.

In the case of Swern oxidation for example, it can be carried out according to the method described in Jikken Kagaku Koza (fourth edition) Vol. 23, Yuki Gosei V, Sanka Hanno, Maruzen Co., Ltd., pp. 298-346. The reaction solvent is not limited in particular as long as it does not inhibit the reaction and dissolves the starting substances to some extent and examples thereof include dimethyl sulfoxide, tetrahydrofuran, toluene, methylene chloride, chloroform, ethyl acetate, water and a mixed solvent thereof. As an oxidizing agent acting as an activator of dimethyl sulfoxide, oxalyl chloride, trifluoroacetic anhydride, acetic anhydride, cyclohexylimide, phosphorus pentoxide or the like is used at a ratio between a two-times molar amount and a large excess amount with respect to compound (a-6). The reaction temperature is not limited in particular but it is ordinarily between −70° C. and room temperature. The reaction time is not limited in particular but it is ordinarily between 3 and 10 hours, preferably between 3 and 5 hours. The aldehyde compound can be simply purified by converting it into a sodium bisulfite adduct and also can be easily regenerated according to the method described in D. P. Kjell et al., "A Novel, Nonaqueous Method for Regeneration of Aldehydes from Bisulfite Adducts" J. Organic. Chemistry. 64, 5722-5724 (1999). The sodium bisulfite adduct can be obtained by allowing an aldehyde compound to react with an aqueous sodium bisulfite solution for example, in an organic solvent such as ethanol, ethyl acetate or methanol or in a mixed solvent thereof. Sodium bisulfite is used at a ratio between one equivalent and a large excess amount with respect to the aldehyde compound. The reaction temperature is not limited in particular but it is ordinarily between 10 and 40° C., and preferably it is room temperature.

The reaction time is not limited in particular but it is ordinarily between 1 and 48 hours, preferably between 12 and 24 hours.

The thus obtained sodium bisulfite adduct is treated with a base (aqueous solution) such as potassium carbonate, sodium carbonate, sodium hydroxide and potassium hydroxide in an organic solvent such as ethanol, ethyl acetate and methanol, or in a mixed solvent thereof, so as to obtain an aldehyde compound. A base is used at a ratio between one equivalent and a large excess amount with respect to the sodium bisulfite adduct. The reaction temperature is not limited in particular, but it is ordinarily between 10 and 40° C., and preferably it is room temperature.

The reaction time is not limited in particular, but it is ordinarily between 1 and 48 hours, preferably between 12 and 24 hours. Compound (a) can be used after purified or without being purified to prepare compounds (i).

In the meantime, the compound (b) used in Step (1) can be obtained, for example, by the following Steps (B-1) to (B-6).

Step (B-1)

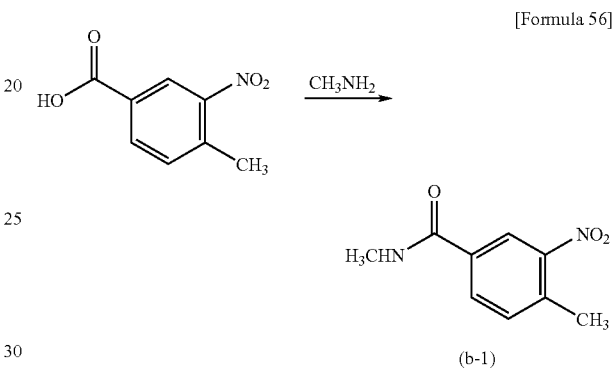

[Formula 56]

Step (B-1) is a step of obtaining a compound represented by the above formula (b-1) by subjecting 3-nitro-4-methylbenzoic acid and methylamine to condensation reaction.

This reaction can be performed in similar conditions as commonly used such as those described in the following documents. Examples of the conventionally known methods include Rosowsky, A.; Forsch, R. A.; Moran, R. G.; Freisheim, J. H.; J. Med. Chem. 34 (1), 227-234 (1991), Brzostwska, M.; Brossi, A.; Flippen-Anderson, J. L.; Heterocycles, 32 (10), 1969-1972 (1991), Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Vorman, R. L.; Reusser, F.; ALthaus, I. W.; Downey, K. M, So, A. G.; Resnick, L.; Tarpley, W. G.; Aristoff, P. A.; J. Med. Chem. 37 (7), 999-1014 (1994).

The condensing agent may include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC (N,N-dicyclohexylcarbodiimide) and diethylphosphoryl cyanide. An organic base, for example, triethylamine between one equivalent and a large excess amount for 3-nitro-4-methyl benzoic acid may be also added if necessary. The reaction solvent is not limited in particular as long as it does not inhibit the reaction and dissolves the starting substances to some extent and specific examples thereof include tetrahydrofuran, 1,4-dioxane, ethyl acetate, methyl acetate, dichloromethane, chloroform, N,N-dimethylformamide, toluene and xylene. The reaction temperature varies depending on starting materials and a solvent used and it is not particularly limited but it is preferably between a temperature on ice and a reflux temperature of the solvent. The reaction time is not particularly limited but it is ordinarily between 0.5 and 48 hours, preferably between 0.5 and 24 hours. The obtained compound (b-1) can be used in the next step after purified by an ordinary method or without being purified.

Step (B-2)

[Formula 57]

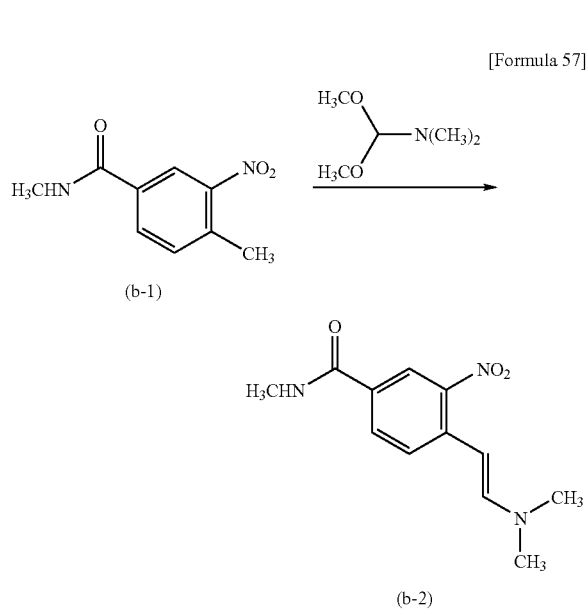

Step (B-2) is a step of obtaining a compound (b-2) by reacting a compound represented by the above formula (b-1) and dimethyl formamide dimethyl acetal.

This step can be performed by a synthetic process well-known for those skilled in the art, for example, in similar conditions as described in Coe, J. W.; Vetelino, M. G.; Bradlee, M. J.; Tetrahedron Lett. 37 (34), 6045-6048 (1996). The reaction solvent is not limited in particular as long as it does not inhibit the reaction and dissolves the starting substances to some extent and, for example, methanol, ethanol, tetrahydrofuran, N,N-dimethylformamide, methylene chloride, 1,2-dichloroethane can be used. The reaction temperature is ordinarily between room temperature and a reflux temperature of the solvent, and preferably between room temperature and 100° C. The reaction time is not limited in particular but it is ordinarily between 1 and 72 hours, preferably between 1 and 48 hours. The obtained compound (b-2) can be used in the next step after purified by an ordinary method or without being purified.

Step (B-3)

[Formula 58]

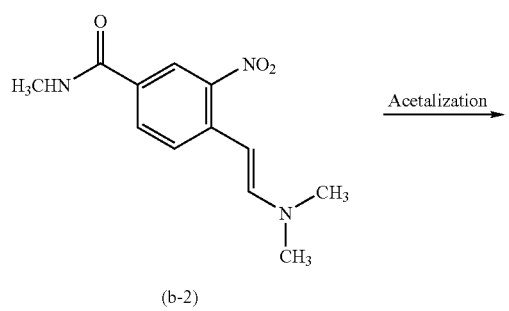

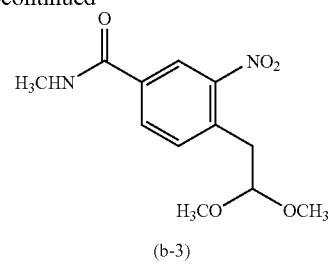

Step (B-3) is a step of obtaining a compound represented by the above formula (b-3) by acetalizing a compound represented by the above formula (b-2).

The acetalization of this step can be performed by a process well-known for those skilled in the art, for example, in similar conditions as described in Coe, J. W.; Vetelino, M. G.; Bradlee, M. J.; Tetrahedron Lett. 37 (34), 6045-6048 (1996). The reaction temperature is ordinarily between room temperature and a reflux temperature of the solvent, and preferably between room temperature and 100° C. The reaction time is not limited in particular but it is ordinarily between 1 and 72 hours, preferably between 1 and 48 hours. The obtained compound (b-3) can be used in the next step after purified by an ordinary method or without being purified.

Step (B-4)

[Formula 59]

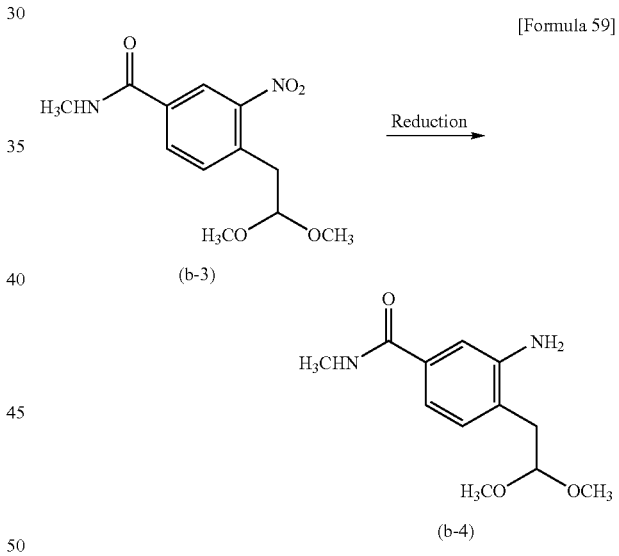

Step (B-4) is a step of obtaining a compound represented by the above formula (b-4) by reducing a compound represented by the above formula (b-3).

The reduction reaction in this step may include conventionally known methods and examples thereof include reduction by the catalytic hydrogenation using Raney nickel or precious metal catalysts such as palladium, ruthenium, rhodium and platinum. Preferred examples in this case include methods using palladium or palladium hydroxide. Alternatively, reduction reaction by iron under neutral conditions with ammonium chloride may be exemplified. The solvent is not limited in particular as long as it does not inhibit the reaction and dissolves the starting substances to some extent and for example, methanol, ethanol, tetrahydrofuran, N,N-dimethylformamide, methylene chloride, 1,2-dichloroethane can be used. The reaction conditions are not particularly limited and the reaction can be carried out at a temperature between room temperature and a reflux temperature of the solvent at a pressure between an atmospheric pressure and 15 MPa, preferably between room temperature and 60° C. at a pressure between an atmospheric pressure and 0.5 MPa. The reaction time is not limited in particular but it is ordinarily between 1 and 48 hours, preferably between 1 and 24 hours. The obtained compound (b-4) can be used in the next step after purified by an ordinary method or without being purified.

Step (B-5)

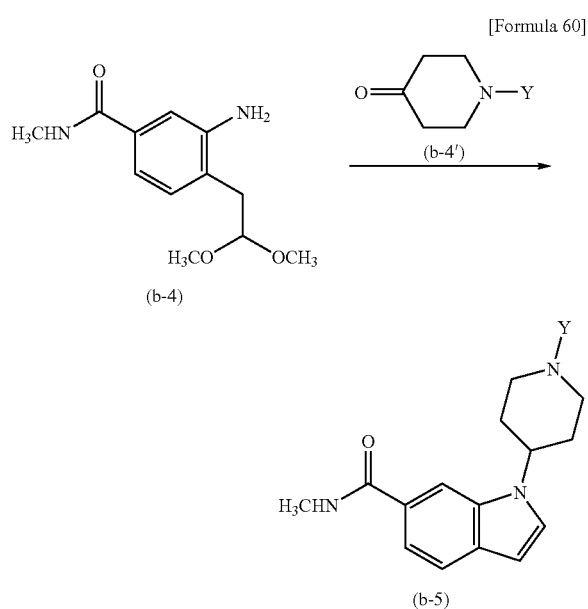

wherein Y represents a protecting group of the secondary amine.

Step (B-5) is a step of obtaining a compound represented by the above formula (b-5) by subjecting the compound represented by the above formula (b-4) and the compound represented by the above formula (b-4') to reductive amination reaction and then performing a ring closure reaction.

The protecting group of a secondary amine represented by Y may include conventionally known groups and examples thereof include a benzyloxycarbonyl group, a tert-butoxy carbonyl group. The reductive amination reaction can be performed in similar conditions as ordinarily used and includes, for example, reductive amination reaction with a reducing agent such as borane and borohydride complex compounds and catalytic reduction reaction under a hydrogen atmosphere using a metal catalyst. Examples of a reductive amination reaction using a borohydride complex compound includes methods described in publications such as Emerson, W. S.; Organic Reactions, 4, 174 (1948), Lane, C. F.; Synthesis, 127 (1974), Abdel-Magid, A. F.; Carson, K. G.; Harris, B. D.; Maryanoff, C. A. and Shah, R. D.; Journal of Organic Chemistry, 61, 3849 (1996).

As a borohydride complex compound, for example, sodium borohydride, sodium cyanoborohydride, sodium triacetoxyborohydride can be used. When a borohydride complex compound is used as a reducing agent, the solvent is not particularly limited as long as it does not inhibit the reaction and dissolves the starting substances to some extent but examples thereof include methanol, ethanol, tetrahydrofuran, N,N-dimethylformamide, methylene chloride, 1,2-dichloroethane. This reaction can provide preferable results such as improvement in the yield by performing the reaction in the presence of an acid. The acid is not particularly limited and preferred examples thereof include mineral acids such as hydrochloric acid, organic acids such as acetic acid, and Lewis acids such as zinc chloride, a boron trifluoride diethyl ether complex and titanium (IV) isopropoxide. The acid can be also used as a solvent.

Compound (b-4') is used at a ratio of 0.8 to 2.5 equivalents, and preferably 1 to 1.5 equivalents, with respect to compound (b-4). The borohydride complex compound is used at a ratio of 1 to 3 equivalents, preferably 1 to 1.5 equivalents, with respect to compound (b-4). The reaction temperature varies depending on starting materials and a solvent used and it is not particularly limited but it is ordinarily between −78° C. and a reflux temperature of the solvent, and preferably between a temperature on ice and room temperature. The reaction time is not particularly limited but it is ordinarily between 0.5 and 48 hours, preferably between 0.5 and 12 hours.

When a catalytic reduction reaction is carried out under a hydrogen atmosphere, the solvent used is not particularly limited, as long as it does not inhibit the reaction and examples of the solvent include methanol, ethanol, tetrahydrofuran and 1,4-dioxane. Examples of the metal catalyst used for the reaction include palladium, platinum oxide and Raney nickel. The reaction conditions are not particularly limited and the reaction can be carried out at a temperature between room temperature and a reflux temperature of the solvent at a pressure between an ordinary pressure and 15 MPa, preferably between room temperature and 60° C. at a pressure between an ordinary pressure and 0.5 MPa. The reaction time is not limited in particular, but it is ordinarily between 1 and 48 hours, preferably between 1 and 24 hours.

The ring closure reaction can be carried out, for example, in similar conditions as described in Coe, J. W.; Vetelino, M. G.; Bradlee, M. J.; Tetrahedron Lett., 37 (34), 6045-6048 (1996), Arai, E.; Tokuyama, H.; Linsell, M. S.; Fukuyama, T.; Tetrahedron Lett., 39 (1), 71-74 (1998), Tishler, A. N., Lanza, T. J.; Tetrahedron Lett., 27 (15), 1653 (1986), and Sakamoto, T.; Kondo, Y.; Yamanaka, H.; Chem. Pharm. Bull., Vol. 34, P. 2362 (1986).

The reaction solvent is not limited in particular as long as it does not inhibit the reaction and dissolves the starting substances to some extent, but specifically it can be performed, for example, using a suitable acid between one equivalent and a large excess amount in water or in water with an organic solvent such as methanol, ethanol, tetrahydrofuran, 1,4-dioxane, benzene, toluene. Examples of the acid include acetic acid, hydrogen chloride, hydrochloric acid, hydrobromic acid, sulfuric acid, nitric acid, trifluoroacetic acid, p-toluenesulfonic acid, p-toluenesulfonic acid-pyridinium salt and camphorsulfonic acid. The reaction time is not limited in particular but it is ordinarily between 1 and 24 hours, preferably between 1 and 24 hours. The obtained compound (b-5) can be used in the next step after purified by an ordinary method or without being purified.

Step (B-6)

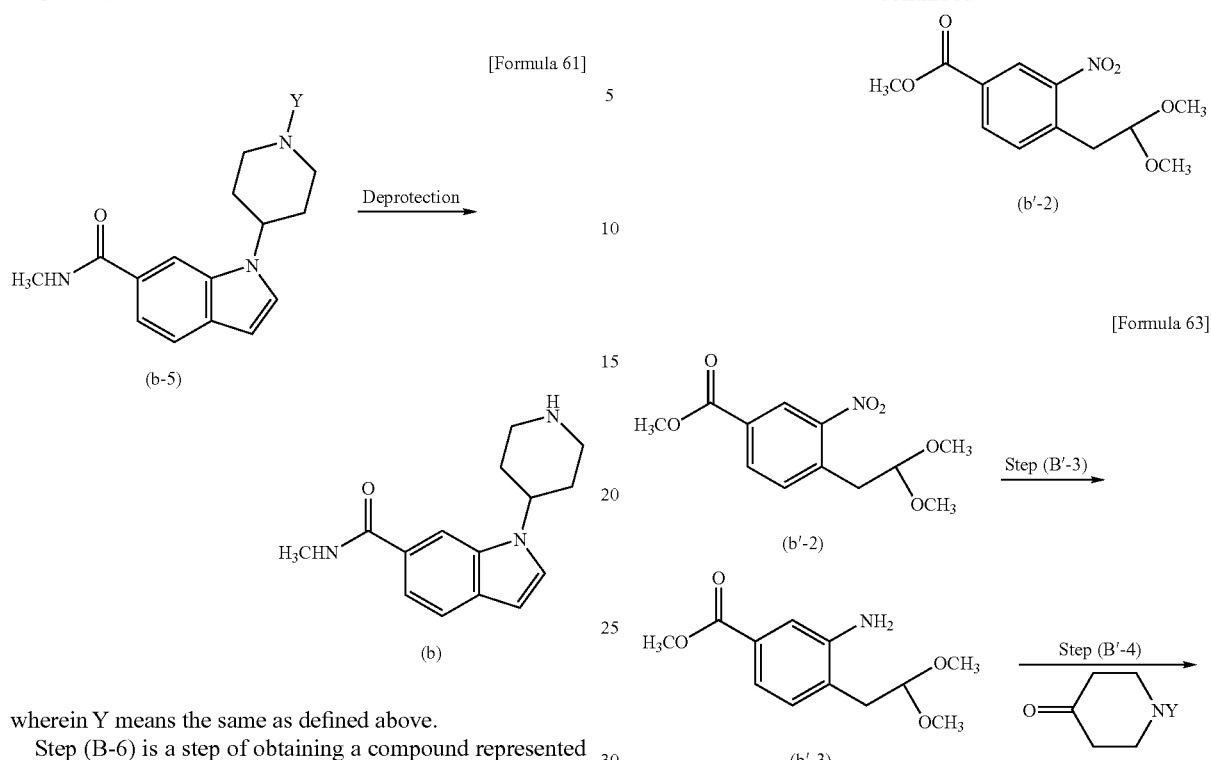

wherein Y means the same as defined above.

Step (B-6) is a step of obtaining a compound represented by the above formula (b) by deprotecting the protecting group of the secondary amine of the compound represented by the above formula (b-5).

The deprotection reaction can be carried out under the similar conditions as those commonly used for eliminating a protecting group for an amino compound, for example, in similar conditions as described in publications such as T. W. Green and P. G. M. Wuts, "Protective groups in Organic Chemistry, Second Edition", John Wiley & Sons (1991), pp. 309-405. When Y is a benzyloxycarbonyl group, for example, the protecting group is deprotected by hydrogenolysis using palladium on carbon as a catalyst in a solvent such as an alcohol and tetrahydrofuran to obtain compound (b).

The obtained compound (b) can be used in the next step after purified by an ordinary method or without being purified.

Compound (b) can be also obtained by the following steps (B'-1) to (B'-6) and the above step (B-6) in addition to the above process.

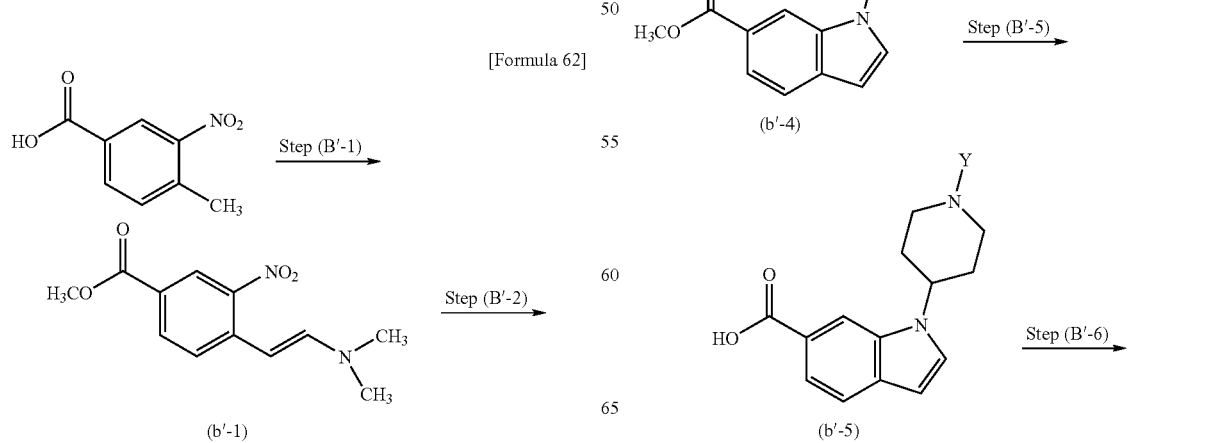

-continued

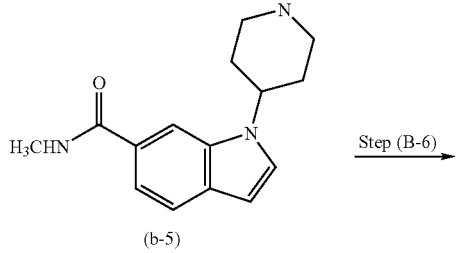

(b-5)

Step (B-6) →

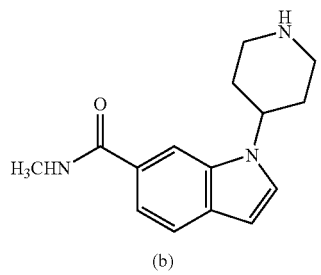

(b)

Step (B'-1)

Step (B'-1) is a step of obtaining a compound (b'-1) by reacting 3-nitro-4-methylbenzoic acid and dimethyl formamide dimethyl acetal. This step can be performed in similar conditions as in the above Step (B-2).

Step (B'-2)

Step (B'-2) is a step of obtaining a compound (b'-2) by acetalizing compound (b'-1). This step can be performed in similar conditions as in the above Step (B-3).

Step (B'-3)

Step (B'-3) is a step of obtaining a compound (b'-3) by reducing compound (b'-2). This step can be performed in similar conditions as in the above Step (B-4).

Step (B'-4)

Step (B'-4) is a step of obtaining compound (b'-4) by reacting compound (b'-3) and compound (b-4'). This step can be performed in similar conditions as in the above Step (B-5).

Step (B'-5)

Step (B'-5) is a step of obtaining compound (b'-5) by hydrolysing compound (b'-4).

This step can be carried out in similar conditions as those described in, for example, Matassa, V. G.; Brown, F. J.; Bernstein, P. R.; Shapiro, H. S.; Maduskuie, T. P. J.; Cronk, L. A.; Vacek, E. P.; Yee, Y. K.; Snyder, D. W.; Krell, R. D.; Lerman, C. L.; Maloney, J. J.; J. Med. Chem., 33 (9), 2621-2629 (1990). Specifically, for example, a base (aqueous solution) such as sodium hydroxide is added to a solution containing compound (b'-4) and the mixture is then stirred for several hours to 1 day and thereafter, the resultant mixture is treated with an acid such as citric acid, so as to obtain compound (b'-5). The reaction solvent is not limited in particular as long as it does not inhibit the reaction and dissolves the starting substances to some extent and examples thereof include methanol, ethanol, 2-propanol, tetrahydrofuran, 1,4-dioxane and water. The base is not particularly limited and examples thereof include sodium hydroxide, potassium hydroxide, and lithium hydroxide. The amount of the base used is between one equivalent and a large excess amount and preferably between one equivalent and 20 equivalents, with respect to compound (b'-4). The reaction time is not limited in particular, but it is ordinarily between 1 and 24 hours, preferably between 1 and 6 hours. The reaction temperature varies depending on starting materials and a solvent used and it is not particularly limited but it is ordinarily between −78° C. and a reflux temperature of the solvent, and preferably between a temperature on ice and room temperature.

The obtained compound (b'-5) can be used in the next step after purified by an ordinary method or without being purified.

Step (B'-6)

Step (B'-6) is a step of obtaining compound (b-5) by subjecting compound (b'-5) and methylamine to condensation reaction. This step can be performed in similar conditions as in the above Step (B-1).

In the meantime, compound (i) can be also obtained by the following steps (C-1) to (C-4).

[Formula 65]

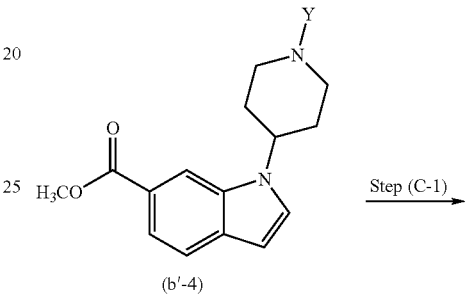

(b'-4)

Step (C-1) →

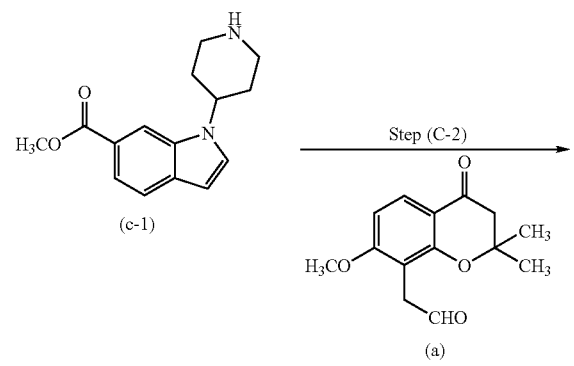

(c-1)

Step (C-2) →

(a)

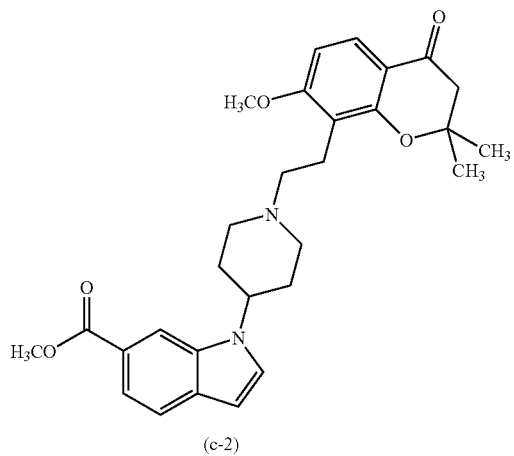

(c-2)

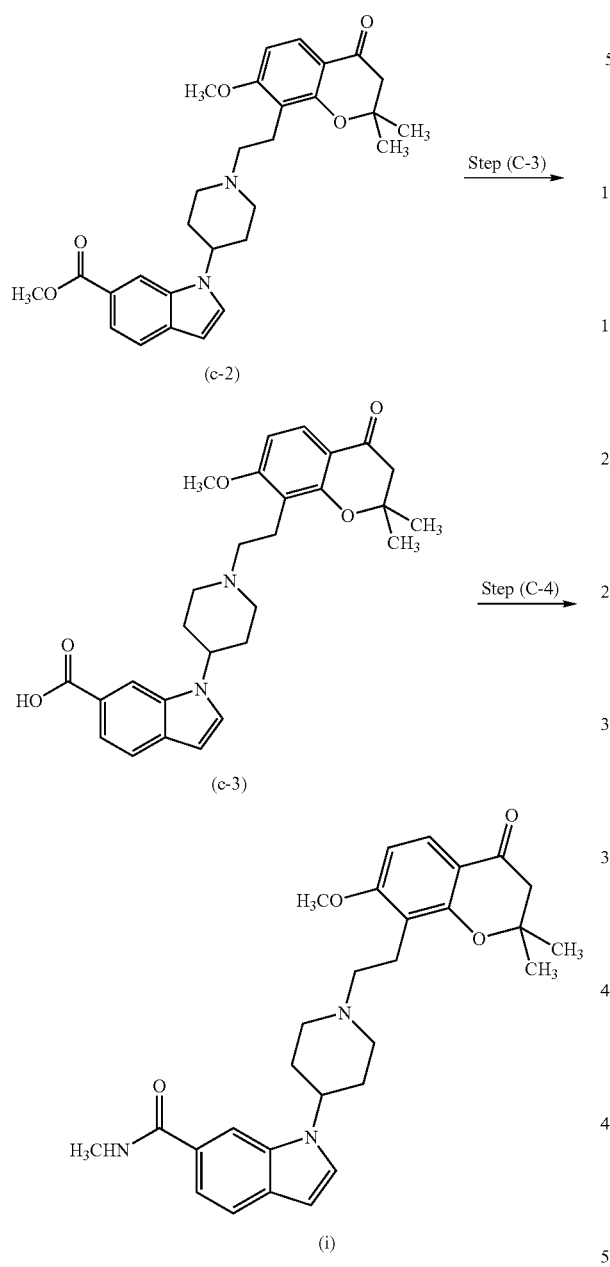

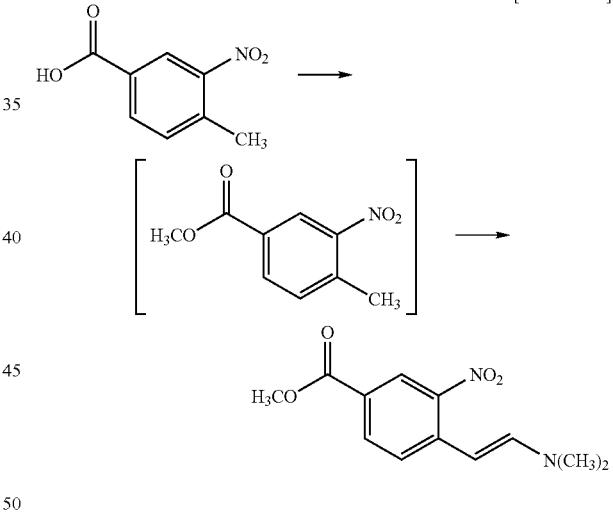

Step (C-1)

Step (C-1) is a step of obtaining a compound represented by the above formula (c-1) or a salt thereof by deprotecting a protecting group of the secondary amine of a compound represented by the above formula (b'-4) wherein Y represents a protecting group of the secondary amine. The salt may be any conventionally known salt which is pharmacologically acceptable, but preferably it is hydrochloride.

This step can be performed in similar conditions as in the above Step (B-6).

Step (C-2)

Step (C-2) is a step of obtaining a compound represented by the above formula (c-2) by coupling a compound represented by the above formula (c-1) and a compound represented by the above formula (a).

This step can be performed in similar conditions as in the above (1).

Step (C-3)

Step (C-3) is a step of obtaining a compound represented by the above formula (c-3) by hydrolysing a compound represented by the above formula (c-2).

This step can be performed in similar conditions as in the above Step (B'-5).

Step (C-4)

Step (C-4) is a step of obtaining a compound represented by the above formula (i) by subjecting a compound represented by the above formula (c-3) and methylamine to condensation reaction.

This step can be performed in similar conditions as in the above Step (B-1).

Hereinbelow, the present invention is specifically described by way of Examples but the present invention is not limited to these Examples. The "room temperature" as used in this specification means a range of 20 to 30° C. and preferably it means 25° C.

PRODUCTION EXAMPLE 1

Synthesis of methyl 4-(2-dimethylamino)vinyl-3-nitrobenzoate 570.0 g (3.15 mol) of 4-methyl-3-nitrobenzoic acid and 3420 mL of N,N-dimethylformamide (hereinbelow referred to as "DMF") were added to a 10 L four-necked flask under a nitrogen atmosphere and stirred. Subsequently, 1334 mL (1197 g, 9.44 mol) of N,N-dimethylformamide dimethylacetal was added portionwise divided into three to the reaction mixture. After the reaction mixture was stirred at room temperature for about 1 hour, the reaction vessel was heated in an oil bath (83° C.). About 15 hours later, after the progress of the reaction was confirmed by HPLC, heating was stopped and the vessel was cooled with an ice-water bath so that the inner temperature reached 28° C.

9120 mL of water was added to a 15 L four-necked flask and cooled and stirred in a flask on an ice-water bath to prepare cold water. The above reaction mixture was poured into this for 6 minutes. After the remaining reaction mixture was rinsed out with 100 mL of DMF, the ice-water bath was removed and the reaction mixture was stirred at room temperature for 76 minutes. The precipitated solid was obtained by filtration, and the remaining solid was rinsed out with 1.5 L of water and further washed with 1.5 L of water. The obtained rough crystals were added to a 20 L stainless steel container, 6840 mL of methanol was added thereto and the reaction mixture was stirred with a mechanical stirrer at room temperature for 65 minutes. Crystals were obtained by filtration and washed with 1140 mL of methanol. The obtained crystals were dried under reduced pressure at 40° C. and 668.7 g of the title compound was obtained as a red solid.

Yield: 84.9%

$^1$H-NMR (400 MHz, CDCl$_3$) δ (ppm): 2.99 (s, 6H), 3.90 (s, 3H), 5.92 (d, J=13.3 Hz, 1H), 7.16 (d, J=13.3 Hz, 1H), 7.47 (d, J=8.6 Hz, 1H), 7.90 (dd, J=8.6, 1.8 Hz, 1H), 8.49 (d, J=1.8 Hz, 1H).

PRODUCTION EXAMPLE 2

Synthesis of methyl 4-(2,2-dimethoxyethyl)-3-nitrobenzoate

[Formula 68]

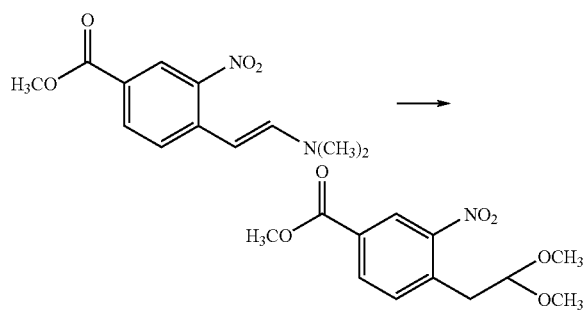

522 g (2.09 mol) of methyl 4-(2-dimethylamino)vinyl-3-nitrobenzoate was added to a 10 L four-necked flask under a nitrogen atmosphere and 3500 mL of methanol was added thereto. A solution of sulfuric acid in methanol (concentrated sulfuric acid: 266 g, methanol: 676 mL) was added to this solution at room temperature over 13 minutes. The reaction vessel was heated in an oil bath (55° C.), and after the inner temperature exceeded 40° C., the reaction mixture was heated and stirred for about 4 hours, and then the reaction vessel was cooled with an ice-water bath. After 193.5 mL of triethylamine was added to the reaction mixture, this solution was concentrated in vacuo and 6000 mL of toluene and 2620 mL of water were added to the concentrated residue. The reaction mixture was filtered through Hyflo Super-Cel with a Buchner funnel and the Buchner funnel was washed with 525 mL toluene to remove insoluble matters. This filtrate was transferred to a 20 L separating funnel, and the aqueous layer was discarded. After the organic layer was washed with 1305 mL of water, it was concentrated in vacuo (bath temperature: 40° C.) and a brown oil containing 625.7 g of the title compound was obtained.

$^1$H-NMR (CDCl$_3$) δ (ppm): 3.28 (d, J=5.3 Hz, 2H), 3.45 (s, 6H), 3.96 (s, 3H), 4.57 (t, J=5.3 Hz, 1H), 7.51 (d, J=8.1 Hz, 1H), 8.16 (dd, J=8.1, 1.8 Hz, 1H), 8.53 (d, J=1.8 Hz, 1H).

PRODUCTION EXAMPLE 3

Synthesis of methyl 3-amino-4-(2,2-dimethoxyethyl)benzoate

[Formula 69]

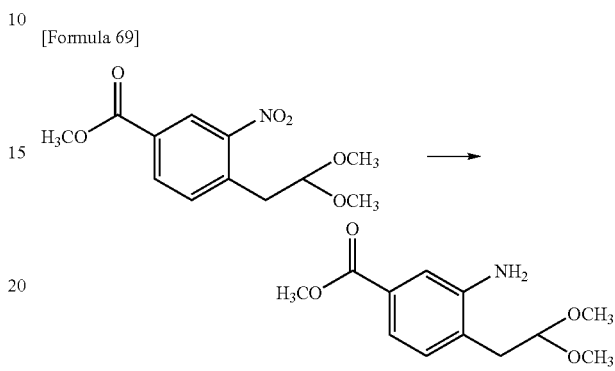

Methyl 4-(2,2-dimethoxyethyl)-3-nitrobenzoate (content=562 g, 2.09 mol assuming the yield of the prior step to be 100%) was rinsed into a 7 L autoclave with 3000 mL of methanol. 56.2 g of palladium on carbon (10% (50% water content)) was added to this solution and 2055 mL of methanol was further added. Chiller water was circulated through the jacket of the reactor, and the reaction was started and the reaction mixture was stirred for 2.5 hours while the hydrogen pressure was controlled between 0.1 and 0.3 MPa (inner temperature: 14 to 23° C.). The reaction mixture was drawn out of the reactor and rinsed out with 320 mL of methanol. The catalyst was removed by filtration with Hyflo Super-Cel and the catalyst was washed with 1080 mL of methanol. When the filtrate was concentrated (bath temperature: 40° C.), crystallized title compound crystallized. These crystals were added with 265 mL of 1,2-dimethoxyethane (hereinbelow referred to as "DME") and warmed at 40° C. for dissolution, and then the solution was concentrated again to obtain a brown oil containing the title compound.

Amount: 572.4 g $^1$H-NMR (CDCl$_3$) δ (ppm): 2.91 (d, J=5.3 Hz, 2H), 3.38 (s, 6H), 3.88 (s, 3H), 4.17 (br, 2H), 4.50 (t, J=5.3 Hz, 1H), 7.11 (d, J=7.6 Hz, 1H), 7.3-7.45 (m, 2H).

PRODUCTION EXAMPLE 4

Synthesis of methyl 1-(1-benzyloxycarbonylpiperidin-4-yl)-1H-indole-6-carboxylate

[Formula 70]

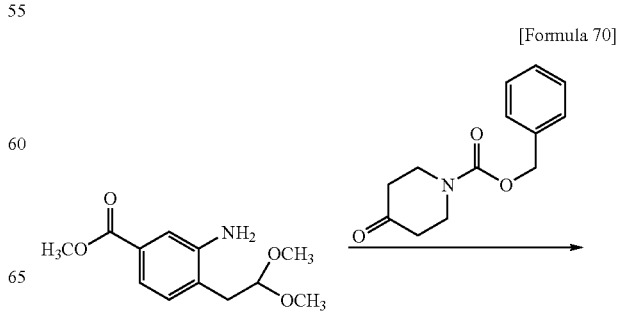

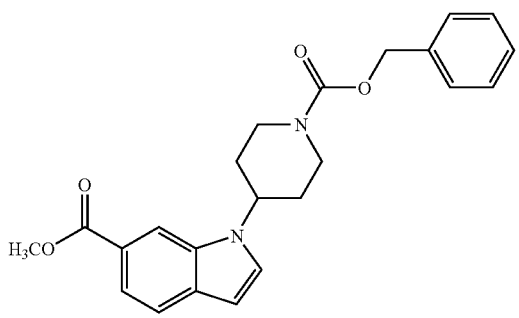

475 g (1.99 mol) of methyl 3-amino-4-(2,2-dimethoxyethyl)benzoate was added to a 15 L four-necked round bottom flask and rinsed in with 3000 mL of acetic acid under a nitrogen atmosphere. 695 g (2.98 mol) of benzyl 4-oxo-1-piperidinecarboxylate was added to this solution while stirring, and washed in with 800 mL of acetic acid. After the reaction mixture was stirred at room temperature for one hour, it was stirred on an ice-water bath. 631.1 g (2.98 mol) of sodium triacetoxyborohydride divided into 8 portions was added to the reaction mixture while the inner temperature was kept to below 15° C., and the ice-water bath was changed to a water bath and the reaction mixture was stirred for about 3 hours. The reaction mixture was cooled with an ice-water bath again and 3800 mL of water was added into the reaction mixture. The reaction mixture was warmed with an oil bath which had been warmed to 100° C. beforehand, and heating was stopped 6 hours after the time point when the inner temperature had reached 80° C.

The reaction mixture was transferred to a 20 L separating funnel and to this was added 5938 mL of toluene and 2969 mL of water and, after stirring and settling, the aqueous layer was discarded. The organic layer was washed sequentially with 4453 mL and 2969 mL of 0.5 N aqueous sodium hydroxide, 2969 mL of 5% sodium chloride solution twice and 2969 mL of water.

The organic layer was concentrated (bath temperature: 40° C.) and 1025.1 g of a brown oil containing the title compound was obtained.

1017.1 g of this oil was dissolved in 1017 mL of methanol and 800 mg of seed crystals of the title compound were put therein at room temperature. The crystals were filtered off after stirred for about 17 hours and washed with 500 mL of methanol. The crystals were dried in vacuo at 40° C. for about 2.5 hours and 622.2 g of the title compound was obtained as pale yellow crystals.

Yield: 79.3%

$^1$H-NMR (CDCl$_3$) δ (ppm): 1.80-2.05 (m, 2H), 2.05-2.23 (m, 2H), 2.92-3.15 (m, 2H), 3.96 (s, 3H), 4.30-4.60 (m, 3H), 5.18 (s, 2H), 6.58 (dd, J=0.4, 2.8 Hz, 1H), 7.30-7.45 (m, 6H), 7.64 (dd, J=0.4, 8.4 Hz, 1H), 7.80 (dd, J=1.6, 8.4 Hz, 1H), 8.14 (s, 1H).

PRODUCTION EXAMPLE 5

Synthesis of 1-(1-benzyloxycarbonylpiperidin-4-yl)-1H-indole-6-carboxylic acid

[Formula 71]

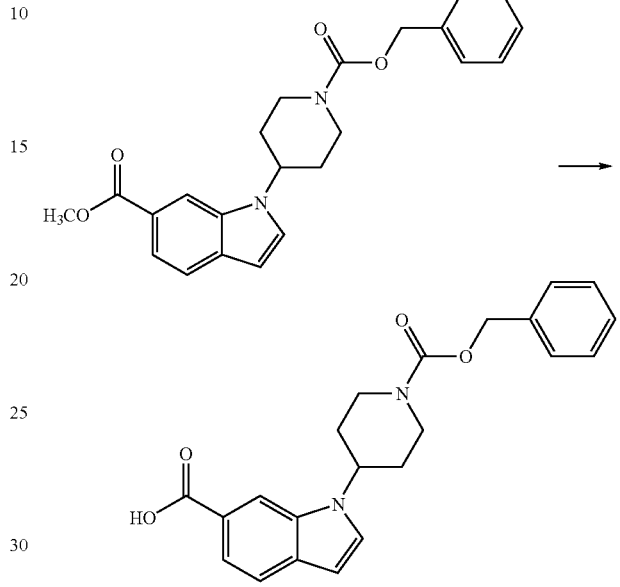

617.0 g (1.57 mol) of methyl 1-(1-benzyloxycarbonylpiperidin-4-yl)-1H-indole-6-carboxylate, 2036 mL of DME and 4072 mL of dimethyl sulfoxide were added to a 20 L four-necked round bottom flask sequentially and stirred while cooling with an ice-water bath. When the temperature of the mixture reached 10° C., 864.7 g of 8% aqueous sodium hydroxide (1.10 molar equivalents, obtained by dissolving 74.4 g of sodium hydroxide in 790 mL of water) was added dropwise to the above solution for 7 minutes. After the dropwise addition was completed, the ice bath was changed to an ice-water bath (24.5° C. to 22.3° C.) and the reaction mixture was stirred for 4 hours and 10 minutes while keeping the temperature of the mixture in a range of 20° C. to 22° C.

The reaction mixture was divided into two portions equally (3.62 L×2) and each of them was subjected to work up in the same way. 3.62 L of the reaction mixture was cooled with an ice-water bath and to this was added 2314 mL of water over 17 minutes and subsequently was added 1543 mL of ethyl acetate. When the mixture's temperature reached 10° C., 420 mL of 2 N hydrochloric acid was added to the reaction mixture to adjust the pH of the aqueous layer to 7. This solution was transferred to a 20 L separating funnel and added with 2314 mL of water and 1543 mL of ethyl acetate and after stirring and settling the aqueous layer was discarded.

This organic layer was combined with the organic layer resulted from work-up of another reaction mixture and washed with 3085 g of 5% sodium chloride solution and 3085 mL of water sequentially. Since crystals precipitated when the vacuum concentration of the organic layer was started, the concentration was stopped and 200 mL of tetrahydrofuran was added to form a solution and the yield was determined by assaying this solution by HPLC. The organic layer was concentrated in vacuo and azeotropic operation was carried out with 2468 mL of toluene (total amount used for twice azeotropic operation) twice under reduced pressure and 1333.6 g of a mixture of yellowish white solid and liquid was obtained.

Title compound content: 566.1 g; Yield: 95.2%

$^1$H-NMR (CDCCl$_3$) δ (ppm): 1.80-2.04 (m, 2H), 2.06-2.21 (m, 2H), 2.94-3.16 (m, 2H), 4.30-4.58 (m, 3H), 5.19 (s, 2H), 6.60 (dd, J=0.8, 3.6 Hz, 1H), 7.30-7.44 (m, 6H), 7.68 (dd, J=0.8, 8.4 Hz, 1H), 7.88 (dd, J=1.6, 8.4 Hz, 1H), 8.22 (s, 1H).

PRODUCTION EXAMPLE 6

Synthesis of 1-(1-benzyloxycarbonylpiperidin-4-yl)-N-methyl-1H-indole-6-carboxamide

[Formula 72]

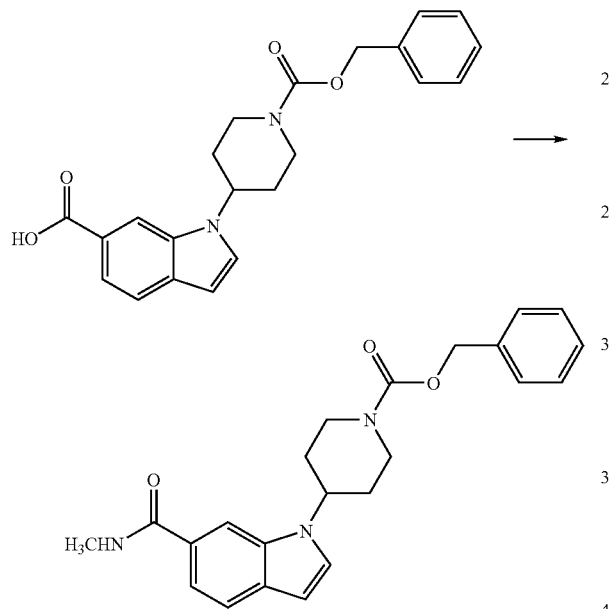

1333.6 g (content 566.1 g, 1.50 mmol) of 1-(1-benzyloxycarbonylpiperidin-4-yl)-1H-indole-6-carboxylic acid and 5950 mL of tetrahydrofuran was added to a 15 L four-necked round bottom flask in stream of nitrogen and stirred at room temperature. 339.5 g of N,N'-carbonyldiimidazole (hereinbelow referred to as "CDI") was added to this solution and 17.4 g of CDT was further added about 1 hour later. The reaction mixture was cooled with an ice-water bath about 1 hour later and when the inner temperature reached 10° C. or less, 407 mL of 40% methylamine aqueous solution was added dropwise over 12 minutes at a time point and the reaction mixture was stirred at the same temperature for about 1.5 hours.

The reaction mixture was divided into two portions equally (organic layer=3740 mL×2, aqueous layer=92 mL×2) and each of them was subjected to work up in the same way. One of the reaction mixture (organic layer=3740 mL; aqueous layer=92 mL) was transferred to a 20 L separating funnel, to this was added 5950 mL of ethyl acetate and 2975 mL of water sequentially and the mixture was stirred, settled and separated. 540 mL of 2 N hydrochloric acid was added to the organic layer and the mixture was stirred and after the pH of the aqueous layer was adjusted to 3 and allowed to be separated. The organic layer was washed with 2975 g of 10% sodium chloride solution, 2975 g of 5% sodium chloride solution and 1488 mL of water sequentially.

The organic layer which had been divided as another portion and subjected to work up was combined and the title compound in 14921.6 g of the organic layer was assayed.

Content when assayed by HPLC: 561.2 g; Yield: 95.9%

$^1$H-NMR (CDCl$_3$) δ (ppm): 1.93 (brs, 2H), 2.04-2.18 (m, 2H), 3.02 (brs, 2H), 4.26-4.60 (m, 3H), 5.18 (s, 2H), 6.58 (dd, J=0.8, 3.2 Hz, 1H), 7.28-7.44 (m, 7H), 7.65 (dd, J=0.4, 8.4 Hz, 1H), 8.10 (s, 1H).

1270 mL of toluene was added to 12774.0 g of this organic layer, concentrated in vacuo (bath temperature: 40° C.) and 1270 mL of toluene was added again to the concentrate to obtain 986.5 g of a yellowish-brown oil after concentration. This substance was used in the following Production Example 7.

PRODUCTION EXAMPLE 7

Synthesis of N-methyl-1-(piperidin-4-yl)-1H-indole-6-carboxamide

[Formula 73]

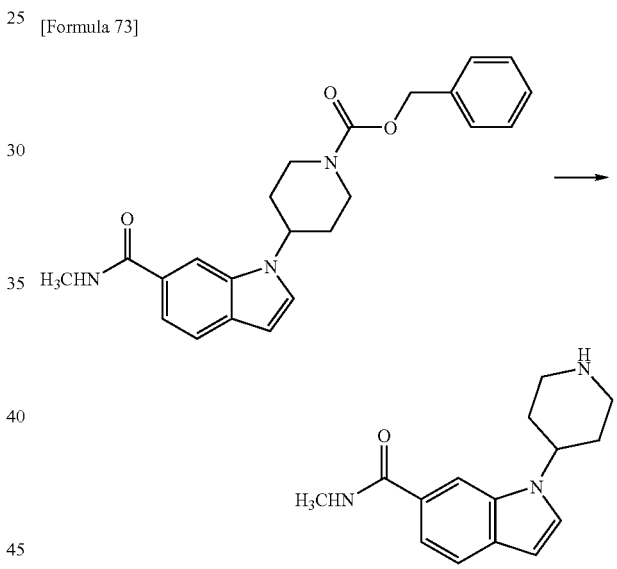

985.5 g (content 489.3 g, 1.25 mmol) of a solution of 1-(1-benzyloxycarbonylpiperidin-4-yl)-N-methyl-1H-indole-6-carboxamide in toluene was added with 2447 mL of tetrahydrofuran and dissolved, and then put into a 7 L autoclave. Next, 2447 mL of methanol and 49 g (50% water content) of 10% palladium on carbon were sequentially added to the reaction mixture. The inside of the reaction vessel was substituted with nitrogen twice and subsequently substituted with hydrogen twice. The reaction mixture was stirred for about 2 hours while the hydrogen pressure was controlled between 0.1 MPa and 0.2 MPa. Pressurization was removed, and the inside of the autoclave was substituted with nitrogen and then opened and the reaction mixture was ejected from the bottom of the reactor. The inside of the autoclave was washed with a mixed solution of methanol/tetrahydrofuran (1/1), and the reaction mixture and the washing were combined. The catalyst was collected by filtration and the filtration cake was washed with methanol/tetrahydrofuran (1/1). The filtrate was concentrated in vacuo and 830.5 g of a brown solution was obtained.

Content: 345.6 g; Yield: 98.0% (Total yield from methyl 1-(1-benzyloxycarbonylpiperidin-4-yl)-1H-indole-6-carboxylate)

799.7 g (content 332.8 g) of the brown solution was added with 1468 mL of DME and concentrated (water bath 40° C.), and added with 1468 mL of DME again and concentrated to obtain 677.0 g of a mixture of a pale yellow solid and a brown solution.

$^1$H-NMR (CDCl$_3$) δ (ppm): 1.88-2.02 (m, 2H), 2.06-2.16 (m, 2H), 2.80-2.92 (m, 2H), 3.22-3.32 (m, 2H), 4.46 (tt, J=4.0, 12.0 Hz, 1H), 6.58 (dd, J=0.8, 3.2 Hz, 1H), 7.36-7.44 (m, 2H), 7.65 (d, J=8.4 Hz, 1H), 8.11 (s, 1H).

PRODUCTION EXAMPLE 8

Synthesis of N-methyl-4-methyl-3-nitrobenzamide

[Formula 74]

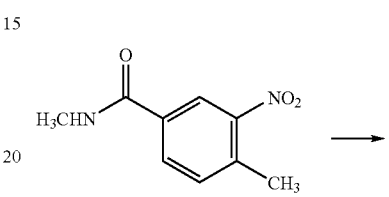

1.83 g (10 mmol) of 3-nitro-4-methyl benzoic acid was dissolved into 18.3 mL of tetrahydrofuran and 2.43 g (15 mmol) of CDI was added to this solution at room temperature under a nitrogen atmosphere. After stirring at room temperature for 1.5 hours, the reaction mixture was cooled with an ice-water bath and 2.33 g (30 mmol) of 40% methylamine aqueous solution was added dropwise thereto. The reaction mixture was stirred while cooled with an ice-water bath for 15 minutes and at room temperature for 2.5 hours.

After diluted with ethyl acetate, the reaction mixture was poured into a 5% NaHCO$_3$ aqueous solution and extracted with ethyl acetate. The organic layer was washed with 0.1 N hydrochloric acid, 5% sodium hydrogen carbonate aqueous solution, 5% sodium chloride aqueous solution and water sequentially, and then dried with anhydrous magnesium sulfate. After separated by filtration, the filtrate was concentrated in vacuo and 1.75 g of the title compound was obtained as a white crystal.

Yield: 90.1%

$^1$H-NMR (400 MHz, CDCl$_3$) δ (ppm): 2.66 (s, 3H), 3.05 (d, J=4.8 Hz, 3H), 6.20 (brs, 1H), 7.44 (d, J=8.4 Hz, 1H), 7.95 (dd, J=2.0, 8.4 Hz, 1H), 8.34 (d, J=2.0 Hz, 1H)

ESI-MS: m/z 217 (M+Na)$^+$

PRODUCTION EXAMPLE 9

Synthesis of 4-(2-dimethylaminovinyl)-N-methyl-3-nitrobenzamide

[Formula 75]

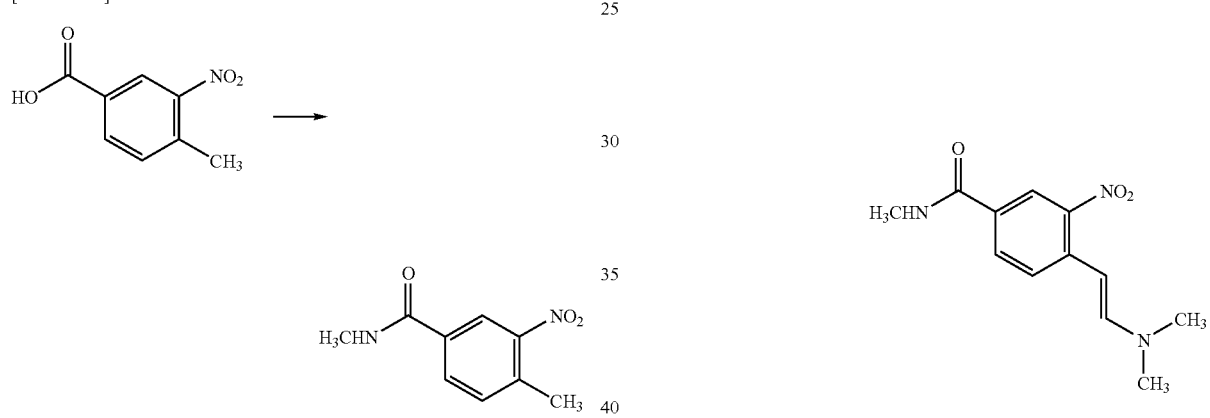

1.65 g (8.49 mmol) of N-methyl-4-methyl-3-nitrobenzamide was dissolved into 9.9 mL of DMF and 6.49 g (50.90 mmol) of N,N-dimethylformamide dimethylacetal was added dropwise to this solution under a nitrogen atmosphere at room temperature, and the reaction mixture was heated and stirred at 80° C. for 46 hours.

After the reaction mixture was concentrated in vacuo, the residue was purified by flash column chromatography (Merck, Silica Gel 60, 230 to 400 mesh; ethyl acetate:heptane, 1:1→2:1). After the fractions containing the object compound were collected and concentrated in vacuo, the residue was purified by flash column chromatography (Fuji silysia, NH-Silica Gel; ethyl acetate:heptane=1:1). The fractions containing the object compound were collected and concentrated in vacuo, and 800.2 mg of the title compound was obtained as dark red crystals.

Yield: 37.8%

$^1$H-NMR (400 MHz, CDCl$_3$) δ (ppm): 2.97 (s, 6H), 3.01 (d, J=4.8 Hz, 3H), 5.94 (d, J=13.2 Hz, 1H), 6.18 (brs, 1H), 7.12 (d, J=13.2 Hz, 1H), 7.49 (d, J=8.4 Hz, 1H), 7.78 (dd, J=2.0, 8.4 Hz, 1H), 8.22 (d, J=2.0 Hz, 1H)

ESI-MS: m/z 272 (M+Na)$^+$

PRODUCTION EXAMPLE 10

Synthesis of 4-(2,2-dimethoxyethyl)-N-methyl-3-nitrobenzamide

[Formula 76]

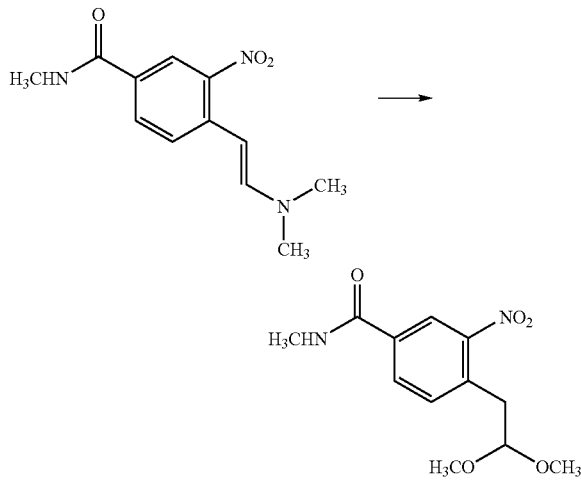

100.0 mg (0.40 mmol) of 4-(2-dimethylaminovinyl)-N-methyl-3-nitrobenzamide obtained in Production Example 9 was dissolved into 0.5 mL of methanol and a solution of 53.8 mg of sulfuric acid in 0.5 mL of methanol was added to this solution at room temperature and heated and stirred at 55° C. for 5 hours.

The reaction mixture was cooled with an ice-water bath and 243 mg (2.40 mmol) of triethylamine was added thereto and then concentrated in vacuo. Water and toluene were added to the residue and extracted with toluene. The organic layer was dried with anhydrous sodium sulfate, separated by filtration, and then concentrated in vacuo to obtain 93.5 mg of the title compound as an orange-red oil.

Yield: 86.9%

$^1$H-NMR (400 MHz, CDCl$_3$) δ (ppm): 3.04 (d, J=4.8 Hz, 3H), 3.27 (d, J=5.2 Hz, 2H), 3.35 (s, 6H), 4.56 (t, J=5.2 Hz, 1H), 6.26 (brs, 1H), 7.50 (d, J=8.0 Hz, 1H), 7.93 (dd, J=2.0, 8.0 Hz, 1H), 8.26 (d, J=2.0 Hz, 1H)

ESI-MS: m/z 291 (M+Na)$^+$

PRODUCTION EXAMPLE 11

Synthesis of 3-amino-4-(2,2-dimethoxyethyl)-N-methylbenzamide

[Formula 77]

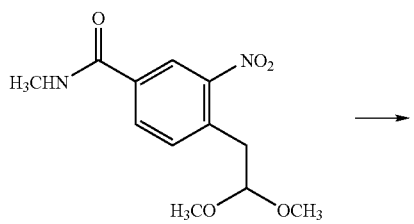

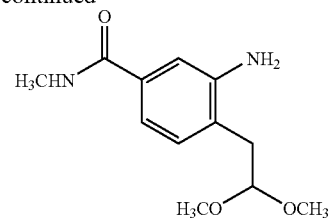

10 mg of 10% palladium on carbon was added to a solution of 93.5 mg (0.35 mmol) of 4-(2,2-dimethoxyethyl)-N-methyl-3-nitrobenzaldehyde obtained in Production Example 10 in 2 mL of methanol and the mixture was subjected to hydrogenation at ambient temperature and atmospheric pressure.

After the reaction was finished, the catalyst was removed by filtration using Hyflo Super-Cel, and the filtrate was concentrated in vacuo to obtain 83.4 mg of the title compound as a pale brown oil.

Yield: 100%

$^1$H-NMR (400 MHz, CDCl$_3$) δ (ppm): 2.88 (d, J=5.2 Hz, 2H), 2.98 (d, J=4.8 Hz, 3H), 3.37 (s, 6H), 4.18 (brs, 2H), 4.49 (t, J=5.2 Hz, 1H), 6.09 (brs, 1H), 7.00 (dd, J=1.6, 8.0 Hz, 1H), 7.08 (d, J=8.0 Hz, 1H), 7.14 (d, J=1.6 Hz, 1H)

ESI-MS: m/z 261 (M+Na)$^+$

PRODUCTION EXAMPLE 12

Synthesis of 1-(1-benzyloxycarbonylpiperidin-4-yl)-N-methyl-1H-indole-6-carboxamide

[Formula 78]

83.4 mg (0.35 mmol) of 3-amino-4-(2,2-dimethoxyethyl)-N-methylbenzamide obtained in Production Example 11 was dissolved into 1.7 mL of acetic acid and 123 mg (0.52 mmol) of benzyl 4-oxo-1-piperidinecarboxylate was added to this solution at room temperature. The reaction mixture was stirred at room temperature under a nitrogen atmosphere. After one hour, the reaction mixture was cooled in a chilled water bath and 117 mg (0.52 mmol) of STAB (sodium triacetoxyborohydride) was added to the reaction mixture and the reaction mixture was stirred at room temperature for 1 hour and 20 minutes. Subsequently the reaction mixture was cooled in a chilled water bath and after 1.7 mL of water was added dropwise to the reaction mixture, the reaction mixture was heated and stirred at 100° C. for 5 hours.

To the reaction mixture was added toluene and extracted. Here 1-(1-benzyloxycarbonylpiperidin-4-yl)-N-methyl-1H-indole-6-carboxamide was precipitated and therefore ethyl acetate was added to the aqueous layer so as to dissolve 1-(1-benzyloxycarbonylpiperidin-4-yl)-N-methyl-1H-indole-6-carboxamide, and subsequently it was neutralized with 5 N sodium hydroxide solution and extracted with ethyl acetate. The organic layer was dried with anhydrous magnesium sulfate which was separated by filtration, concentrated in vacuo and the residue was purified by flash column chromatography (Merck, Silica Gel 60, 230 to 400 mesh; ethyl acetate:heptane=2:1) and 114.9 mg of 1-(1-benzyloxycarbonylpiperidin-4-yl)-N-methyl-1H-indole-6-carboxamide was obtained as a colorless oil.

The obtained oil was dissolved in 0.12 mL of toluene and cyclopentyl methyl ether (0.96 mL) was added dropwise to this solution while stirring at room temperature. This solution was heated and stirred at 50° C., and to this was addressed crystals of 1-(1-benzyloxycarbonylpiperidin-4-yl)-N-methyl-1H-indole-6-carboxamide. Subsequently 0.24 mL of heptane was added dropwise to the reaction mixture while stirring at 50° C., and the reaction mixture was stirred for 10 minutes at 50° C. After this was gradually cooled to room temperature at a rate of 10° C./15 min, the mixture was stirred at 10° C. for one hour. Precipitated crystals were collected by filtration and 99.3 mg of 1-(1-benzyloxycarbonylpiperidin-4-yl)-N-methyl-1H-indole-6-carboxamide was obtained as white crystals.

Yield: 72.7%
$^1$H-NMR (400 MHz, CDCl$_3$) δ (ppm): 1.83-2.02 (br, 2H), 2.04-2.16 (br, 2H), 2.94-3.10 (br, 2H), 3.06 (d, J=4.8 Hz, 3H), 4.30-4.58 (m, 3H), 5.17 (s, 2H), 6.24 (brs, 1H), 6.56 (d, J=3.2 Hz, 1H), 7.28 (d, J=3.2 Hz, 1H), 7.31-7.41 (m, 6H), 7.62 (d, J=8.4 Hz, 1H), 8.05 (s, 1H)
ESI-MS: m/z 414 (M+Na)$^+$

PRODUCTION EXAMPLE 13

Synthesis of 1-(1-ethoxyethoxy)-3-methoxybenzene

[Formula 79]

2600 mL of tetrahydrofuran and 650.4 g (5.24 mol) of 3-methoxyphenol were added to a 15 L four-necked round bottom flask under a nitrogen atmosphere. Subsequently 65.8 g (0.26 mol) of pyridinium p-toluenesulfonate was added to this tetrahydrofuran solution and stirring was started. This mixture was cooled in a temperature-controlled bath set to 8° C. and 760.1 g (10.54 mol) of ethyl vinyl ether was added dropwise to the reaction mixture for about 1.5 hours. The reaction mixture was stirred at the same temperature for 2.7 hours and then the temperature of the temperature-controlled bath was set to 15° C. It was further stirred for about 2 hours from a time point when the inner temperature exceeded 14° C. The temperature of the temperature-controlled bath was set to 8° C., and at a time point when the inner temperature reached almost 10° C., 715.2 g of 8% sodium hydrogen carbonate aqueous solution [prepared by dissolving 57.2 g of sodium hydrogen carbonate in 658 mL of water] was added dropwise to the reaction mixture over 10 minutes. The reaction mixture was transferred to a 20 L separatory funnel and added with 1040 mL of water and added and extracted with 4550 mL of toluene and the organic layer was washed with 1300 mL and 650 mL of water twice. The obtained organic layer was concentrated in vacuo at a bath temperature of 40° C. and a pale yellow oil containing the title compound was obtained.

Amount: 1213.5 g; Content: 1019.3 g; Yield: 99.1%
$^1$H-NMR (400 MHz, CDCl$_3$) δ (ppm): 1.21 (t, J=6.8 Hz, 3H), 1.50 (d, J=5.2 Hz, 3H), 3.50-3.60 (m, 2H), 3.79 (s, 3H), 5.38 (q, J=5.2 Hz, 1H), 6.50-6.66 (m, 3H), 7.13-7.20 (m, 1H).

EXAMPLE 1

Synthesis of ethyl [2-(1-ethoxyethoxy)-6-methoxyphenyl]acetate

[Formula 80]

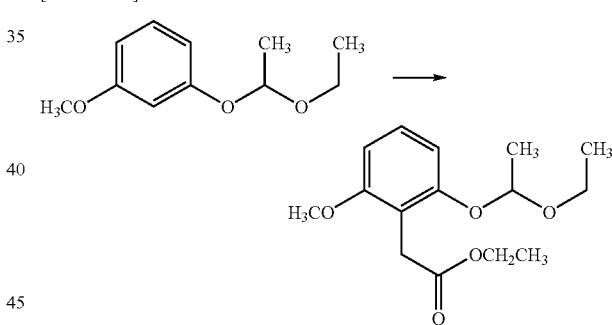

854.0 g of 1-(1-ethoxyethoxy)-3-methoxybenzene (content: 717.4 g (3.66 mol)) was put into a 20 L reactor under a nitrogen atmosphere and rinsed in with 7174 mL of tetrahydrofuran and the mixture was stirred. A coolant which was set to 4° C. was circulated through the jacket of the reactor and 1156 g (4.41 mol) of n-butyllithium [2.71 M, n-hexane solution] was added dropwise for 41 minutes, and the reaction mixture was stirred at the same temperature for about 1.5 hours. The coolant temperature was set to −20° C., and after it was confirmed that the mixture's temperature lowered below −10° C., 417.8 g (2.19 mol) of copper (I) iodide was added portionwise divided into three to the reaction mixture and the reaction mixture was stirred at the same temperature for about 14 hours. The coolant temperature was changed to −90° C. and 702.1 g (4.20 mol) of ethyl bromoacetate was added dropwise to the reaction mixture over 26 minutes and rinsed in with 10 mL of tetrahydrofuran. After the dropwise addition was completed, the reaction mixture was stirred for 44 minutes, and the liquid cooling temperature was changed to −35° C. and the reaction mixture was further stirred for about 1.8 hours. The coolant temperature was changed to −20° C., and the reaction mixture was stirred for one hour after the time point when temperature of the mixture exceeded −20° C. and progress of the reaction was confirmed by HPLC. 1435 mL of 28% ammonium hydroxide solution was added to the reaction mixture at the same temperature for about 30 minutes and the coolant temperature was changed to 25° C. The reaction mixture was added and extracted with 7174 mL of toluene and the organic layer was washed with 1440 mL of 28% ammonium hydroxide solution and 1435 mL×3 water sequentially. The obtained organic layer was added with 127 mL (0.73 mol) of N,N-diisopropylethylamine and concentrated in vacuo to afford a pale orange oil containing the title compound.

Amount: 1122.3 g; Content: 990.7 g; Yield: 96.0%

$^1$H-NMR (400 MHz, CDCl$_3$) δ (ppm): 1.19 (t, J=7.2 Hz, 3H), 1.24 (d, J=7.2 Hz, 3H), 1.47 (d, J=5.2 Hz, 3H), 3.46-3.56 (m, 1H), 3.66-3.82 (m, 3H), 3.80 (s, 3H), 4.14 (q, J=7.2 Hz, 2H), 5.39 (q, J=5.2 Hz, 1H), 6.57 (d, J=8.4 Hz, 1H), 6.70 (d, J=8.8 Hz, 1H), 7.17 (dd, J=8.8, 8.4 Hz, 1H).

EXAMPLE 2

Synthesis of 2-[1-ethoxyethoxy]-6-methoxyphenyl]ethanol

[Formula 81]

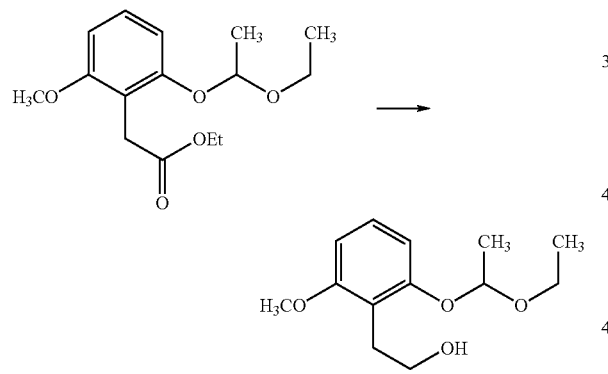

248.8 g (content 213.0 g, 0.754 mol) and 561.6 g (content 495.7 q, 756 mol) of ethyl [2-(1-ethoxyethoxy)-6-methoxyphenyl]acetate, toluene (8504 mL) and DME (2126 mL) were sequentially added to a 15 L four-necked round bottom flask under a nitrogen atmosphere, and stirring was started and the reaction vessel was ice cooled. 1403.7 g (65% toluene solution, 1.8 molar equivalent) of sodium bis(2-methoxyethoxy)aluminum hydride was added dropwise to this solution over 50 minutes. Immediately after the dropwise addition was completed, the ice-water bath was changed to a water bath and the reaction mixture was stirred for 2.5 hours. The water bath was changed to an ice-water bath and 8% (W/W) aqueous sodium hydroxide [prepared by adding 4570 mL of water to 430 g of sodium hydroxide (93.0%)] was added dropwise to the reaction mixture. About 1.5 L was added dropwise for 47 minutes. The reaction mixture was transferred to a 20 L reparatory funnel, and the total amount of the remaining aqueous sodium hydroxide prepared was added thereto, and the aqueous layer was discarded. The organic layer was washed with water (1417 mL×2, 709 mL×1) three times, and then concentrated in vacuo at 40° C. and the title compound contained in the concentrated residue was assayed.

Weight of concentrated residue: 1042.0 g; Content: 563.3 g $^1$H-NMR (400 MHz, CDCl$_3$) δ (ppm): 1.20 (t, J=7.2 Hz, 3H), 1.50 (d, J=5.6 Hz, 3H), 3.00 (t, J=6.8 Hz, 2H), 3.48-3.58 (m, 1H), 3.68-3.90 (m, 3H), 3.82 (s, 3H), 5.42 (q, J=5.6 Hz, 1H), 6.58 (d, J=8.0 Hz, 1H), 6.70 (d, J=8.4 Hz, 1H), 7.13 (dd, J=8.4, 8.0 Hz, 1H).

EXAMPLE 3

Synthesis of ethyl 2-[2-(1-ethoxyethoxy)-6-methoxyphenyl]benzoate

[Formula 82]

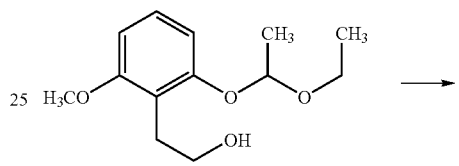

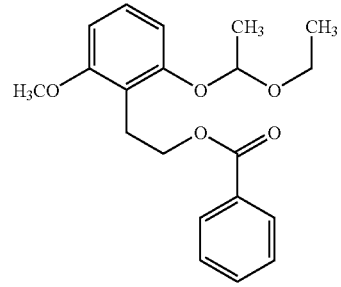

1042.0 g of the concentrated residue of the organic layer obtained in Example 2 was placed in a 15 L four-necked round bottom flask under a nitrogen atmosphere and 8102 mL of toluene, 2025 mL of DME, 304.8 g of triethylamine and 29.2 g of N,N,N',N'-tetramethylethylenediamine were added sequentially. While stirred under ice cold condition, 388.1 g (2.761 mol) of benzoyl chloride was added dropwise to this solution over 40 minutes. After the reaction mixture was stirred at the same temperature for 10 minutes, the ice bath was changed to water bath and the reaction mixture was further stirred for 2.8 hours. The reaction mixture was transferred to a 20 L reparatory funnel and washed with 3544 mL and 709 mL of water. The title compound in 10.84 L of the obtained organic layer was assayed.

Content: 745.0 g $^1$H-NMR (400 MHz, CDCl$_3$) δ (ppm): 1.18 (t, J=7.2 Hz, 3H), 1.48 (d, J=5.2 Hz, 3H), 3.17 (t, J=7.2 Hz, 2H), 3.45-3.56 (m, 1H), 3.66-3.80 (m, 1H), 3.76 (s, 3H), 4.45 (t, J=7.2 Hz, 2H), 5.41 (q, J=5.2 Hz, 1H), 6.55 (d, J=8.4 Hz, 1H), 6.71 (d, J=8.0 Hz, 1H), 7.13 (dd, J=8.4, 8.0 Hz, 1H), 7.36-7.44 (m, 2H), 7.50-7.56 (m, 1H), 7.98-8.06 (m, 2H)

EXAMPLE 4

Synthesis of 2-(2-hydroxy-6-methoxyphenyl)ethyl benzoate

[Formula 83]

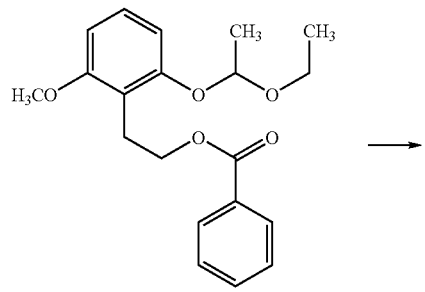

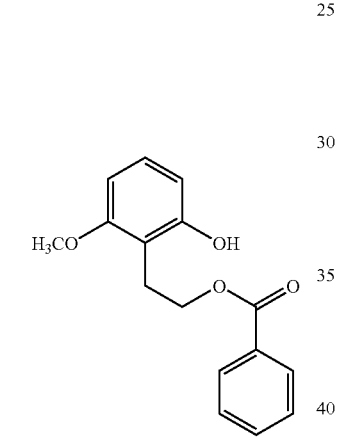

The organic layer obtained in Example 3 was transferred to a 15 L four-necked round bottom flask, added with 2126 mL of tetrahydrofuran, cooled with an ice-water bath and stirred. 1417 mL of 5 N hydrochloric acid was added dropwise to the reaction mixture over 23 minutes, and the reaction mixture was stirred at the same temperature for about one hour. Then the chilled water in the bath was removed and the reaction mixture was stirred for 2.5 hours. The reaction mixture was transferred to a 20 L reparatory funnel and the aqueous layer was discarded. The organic layer was washed with 8% sodium hydrogen carbonate aqueous solution [prepared by adding 1956 mL of water to 170 g of sodium hydrogen carbonate] and washed with water (709 mL×2) twice. The obtained organic layer was concentrated in vacuo at bath temperature of 40° C. to obtain 1463.0 g of a slurry.

The obtained slurry was washed in with 709 mL of tetrahydrofuran into a 10 L four-necked round bottom flask. While being stirred, 5670 mL of a mixed solution of toluene—heptane (1:8) was added dropwise to the reaction mixture over 2.5 hours, and the reaction mixture was further stirred at room temperature for about 14 hours. Precipitated crystals were collected by filtration and washed with 708 mL of a mixed solution of toluene—heptane (1:8). The crystals were dried in vacuo at a bath temperature of 40° C. for about 4.5 hours and the title compound was obtained as white crystals.

Amount: 535.9 g; Yield: 78.4%

$^1$H-NMR (400 MHz, CDCl$_3$) δ (ppm): 3.15 (t, J=7.2 Hz, 2H), 3.79 (s, 3H), 4.45 (t, J=7.2 Hz, 2H), 5.86 (s, 1H), 6.48 (d, J=8.4 Hz, 1H), 6.53 (d, J=8.4 Hz, 1H), 7.09 (dd, J=8.4, 8.4 Hz, 1H), 7.44 (dd, J=7.6, 7.6 Hz, 2H), 7.56 (dd, J=7.6, 7.6 Hz, 1H), 8.04 (d, J=7.6 Hz, 1H).

EXAMPLE 5

Synthesis of 2-(7-methoxy-2,2-dimethyl-4-oxochroman-8-yl)ethyl benzoate

[Formula 84]

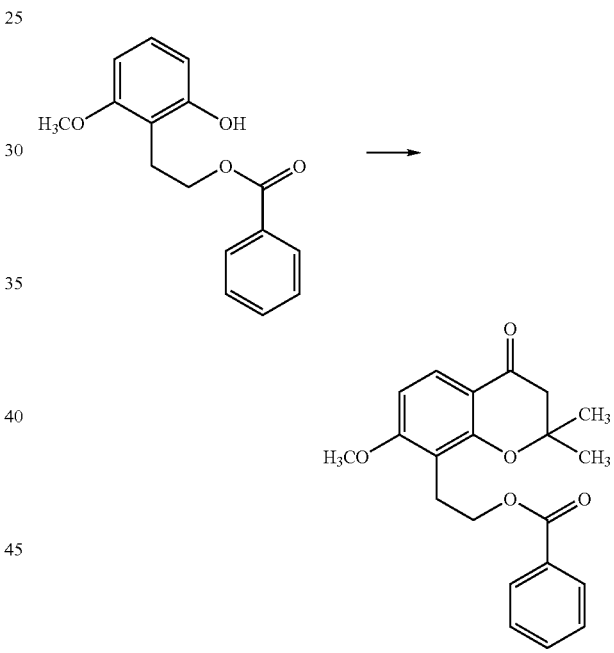

202.2 g (2.020 mol) of 3-methylcrotonic acid and 2 L of methanesulfonic acid were put into a 10 L four-necked round bottom flask and stirred on a 50° C. water bath in stream of nitrogen. 500.0 g (1.836 mol) of 2-(2-hydroxy-6-methoxyphenyl)ethyl benzoate obtained in Example 4 was added to this solution. The reaction mixture was stirred at the same temperature for 1.8 hours and ice cooled. 2.5 L of toluene was added to the reaction mixture and subsequently 5 L of water was added dropwise for about 1 hour. The contents were transferred to a 20 L separatory funnel and allowed to be separated and the aqueous layer was discarded. The organic layer was washed three times with water (5 L×3) and concentrated in vacuo on a 40° C. bath and 846.1 g of the title compound was obtained.

$^1$H-NMR (400 MHz, CDCl$_3$) δ (ppm): 1.39 (s, 6H), 2.62 (s, 2H), 3.13 (t, J=6.8 Hz, 2H), 3.82 (s, 3H), 4.45 (t, J=6.8 Hz, 2H), 6.57 (d, J=8.8 Hz, 1H), 7.38-7.45 (m, 2H), 7.51-7.57 (m, 1H), 7.82 (d, J=8.8 Hz, 1H), 7.98-8.04 (m, 2H).

EXAMPLE 6

Synthesis of 8-(2-hydroxyethyl)-7-methoxy-2,2-dimethylchroman-4-one

[Formula 85]

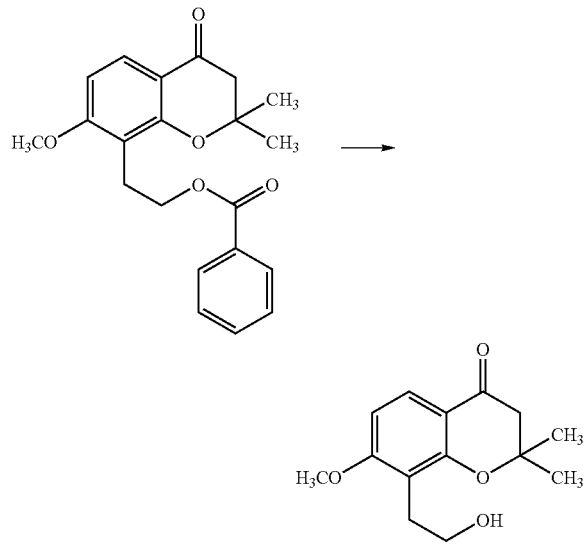

844.9 g of an oily substance obtained in the above Example 5 was dissolved in 2.5 L of tetrahydrofuran and transferred to a 20 L four-necked round bottom flask. 2.5 L of methanol was added to this solution in tetrahydrofuran and the mixture was cooled with a water bath (water temperature: 22° C.). 8% (W/W) aqueous sodium hydroxide [prepared by adding 1678 mL of water to 158 g of sodium hydroxide (93.0%)] was added dropwise over 18 min while being stirred. After the dropwise addition was completed, the water bath was removed, and the reaction mixture was stirred at room temperature over about 3.5 hours. 10 L of water was added dropwise to the reaction mixture for about 1 hour. The reaction vessel was ice cooled and the reaction mixture was stirred for about 1 hour while the inner temperature was kept below 10° C. Precipitated crystals were collected by filtration and washed with 2 L of water and a methanol-water mixture (1:4, 400 mL/1600 mL) sequentially. The obtained crystals were dried under reduced pressure at 40° C. till the weight became constant and 374.7 g of the crude title compound was obtained as a yellowish white solid.

Amount: 374.7 g; Content 305.8 g; Yield: 66.6%

374.7 g of the crude title compound (content 305.8 g) and 2 L of ethyl acetate were added to a 15 L four-necked round bottom flask, and heating and stirring were started with a water bath which was heated to 80° C. 4.116 L of ethyl acetate was added to this suspension and the bath temperature setting was changed to 75° C. After dissolution of the crystals was confirmed, the temperature of the bath was gradually lowered, and seed crystals were added at an internal temperature of 45.3° C. Precipitation of crystals was observed 6 minutes after the addition of the seed crystals. The temperature of the water bath was further lowered, and when the temperature of the mixture lowered below 30° C., 6.116 L of heptane was added to the suspension over about 1 hour and stirred at the same temperature for about 13 hours. The suspension was ice cooled, and crystals were collected by filtration with a Buchner funnel, after 4 hours, and the crystals were washed with 918 mL of ethyl acetate-heptane mixture (1:2). The obtained crystals were dried in vacuo on a 40° C. water bath for about 3 hours and dried in vacuo at room temperature for about 14 hours and the title compound was obtained as a grayish white solid.

Amount: 294.5 g; Content: 275.4 g; Yield: 90.1%
$^1$H-NMR (400 MHz, CDCl$_3$) δ (ppm): 1.45 (s, 6H), 2.68 (s, 2H), 2.96 (t, J=6.8 Hz, 2H), 3.73-3.80 (m, 2H) 3.89 (s, 3H), 6.59 (d, J=8.8 Hz, 1H), 7.81 (d, J=8.8 Hz, 1H).

EXAMPLE 7

Synthesis of 8-(2-hydroxyethyl)-7-methoxy-2,2-dimethylchroman-4-one (recrystallization)

3.71 g (content 3.0 g) of the crude title compound and 45 mL of methyl isobutyl ketone were put into a 100 mL four-necked round bottom flask, and heated and stirred on an oil bath which was heated to 82° C. to form a solution. To this solution was gradually cooled and seed crystals were added when the temperature of the mixture reached 59° C. The temperature setting of the oil bath was lowered by 5° C. every 30 minutes and 30 mL of heptane was added dropwise when the temperature of the mixture was 26.7° C. over about 1 hour. After 18 minutes passed, the suspension was cooled with cold water and crystals were obtained by filtration 1 hour and 50 minutes later. The obtained crystals were washed with 3 mL of methyl isobutyl ketone-heptane mixture (3:2) and dried in vacuo on a 40° C. water bath for about 1 hour and the title compound was obtained as a white solid.

Amount: 2.72 g; Content: 2.64 g; Yield: 87.8%

EXAMPLE 8

Synthesis of (7-methoxy-2,2-dimethyl-4-oxochroman-8-yl)acetaldehyde

[Formula 86]

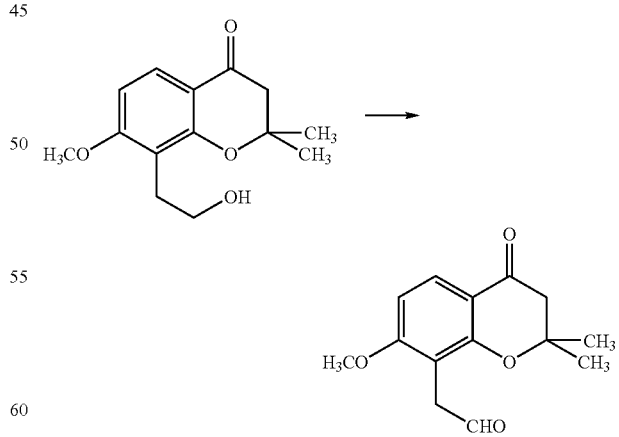

248.3 g (content 232.7 g, 0.930 mol) of 8-(2-hydroxyethyl)-7-methoxy-2,2-dimethylchroman-4-one, 294.0 g (content 274.9 g, 1.098 mol) of the same compound and 7614 mL of ethyl acetate were put in a 15 L four-necked round bottom flask and stirred. Cooling of this suspension was started in a cold bath set to −4° C., and 161.9 g (1.574 mol) of sodium bromide, 508 mL of water, 3.17 g (20.28 mmol) of 2,2,6,6-tetramethylpiperidine oxide were put therein sequentially. After the inner temperature reached 0° C., a mixture of 5.536 mol of sodium hypochlorite solution and 2538 g of 7% (W/W) sodium hydrogen carbonate aqueous solution were added dropwise into the flask over about 2 hours. After the dropwise addition was completed, the temperature of the cooling bus was changed to 0° C. and stirring was continued for 45 minutes. The reaction mixture was transferred to a 20 L separatory funnel and the aqueous layer was discarded. The organic layer was washed with 2030 g of 10% sodium chloride aqueous solution and 2030 mL of water sequentially. The obtained organic layer was concentrated in vacuo (40° C.) and 743.7 g of slurry was obtained. 500 mL of DME was added to the obtained slurry to form a solution and concentrated in vacuo (40° C.) again and 500 mL of DME was added again to the precipitates so that they were dissolved. This solution was transferred to a 5 L four-necked round bottom flask and warmed in a 40° C. water bath. 515 mL of DME was further added and stirred at 183 rpm and about 500 mL of water was cast therein and cooling with an ice-water bath was started 4 minutes later. Seed crystals were added and the mixture was stirred for about 1 hour and 515 mL of water was further added over about 30 minutes. After stirring for about 1.3 hours, 1523 mL of heptane was further added over 1 hour and stirred at the same temperature for about 1 hour or more. Precipitated crystals were collected by filtration, washed with a mixture of DME/water/heptane [about 600 mL, DME/water/heptane=1/1/1.5]. The crystals were dried in vacuo (bath temperature: 40° C.) till the weight became almost constant and the title compound was obtained as a yellowish white solid.

Amount: 478.0 g; Content: 413.9 g; Yield: 82.2%

$^1$H-NMR (600 MHz, DMSO-d$_6$) δ (ppm): 1.34 (s, 6H), 2.70 (s, 2H), 3.63 (s, 2H), 3.83 (s, 3H), 6.80 (d, J=9.0 Hz, 1H), 7.72 (d, J=9.0 Hz, 1H), 9.58 (s, 1H).

EXAMPLE 9

Synthesis of (7-methoxy-2,2-dimethyl-4-oxochroman-8-yl)acetaldehyde

[Formula 87]

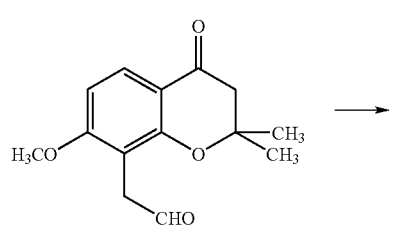

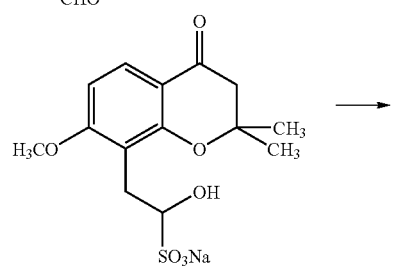

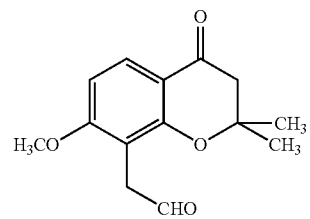

6.54 g (content 6.0 g) of (7-methoxy-2,2-dimethyl-4-oxochroman-8-yl)acetaldehyde, 54 mL of ethanol and 6 mL of ethyl acetate were added into a 200 mL four-necked round bottom flask, and the reaction mixture was stirred at room temperature. A sodium hydrogensulfite aqueous solution (prepared by dissolving 2.51 g to 6 mL of water) was added dropwise to this for 20 minutes. Subsequently 60 mL of ethyl acetate was added dropwise for 1.5 hours and the reaction mixture was stirred at room temperature overnight. Precipitated crystals were collected by filtration, washed with an ethanol/ethyl acetate (1/1) mixed solution (12 mL) and 8.14 g of sodium hydrogensulfite adduct of the title compound was obtained.

Sodium hydrogensulfite adduct of the title compound $^1$H-NMR (600 MHz, DMSO-d$_6$) δ (ppm): 1.35 (s, 3H), 1.36 (s, 3H), 2.66 (s, 2H), 2.88 (dd, J=13.0, 3.0 Hz, 1H), 3.00 (dd, J=13.0, 11.0 Hz, 1H), 3.81 (s, 3H), 4.18 (ddd, J=11.0, 6.0, 3.0 Hz, 1H), 4.35 (d, J=6.0 Hz, 1H), 6.69 (d, J=9.0 Hz, 1H), 7.60 (d, J=9.0 Hz, 1H)

6.0 g of sodium hydrogensulfite adduct of the title compound and 120 mL of ethyl acetate were added to a 300 mL four-necked round bottom flask and stirred. 30 g of 10% potassium carbonate aqueous solution was added to this suspension and the reaction mixture was stirred at room temperature more than 2 hours. The organic layer was separated and the organic layer was washed with 10% sodium chloride solution and water (twice) sequentially. 12 mL of toluene was added to the organic layer, and, after vacuum concentration, dried in vacuo and 3.49 g of the title compound was obtained as a pale yellow solid.

EXAMPLE 10

Synthesis of 1-{1-[2-(7-methoxy-2,2-dimethyl-4-oxochroman-8-yl)ethyl]piperidin-4-yl}-N-methyl-1H-indole-6-carboxamide

[Formula 88]

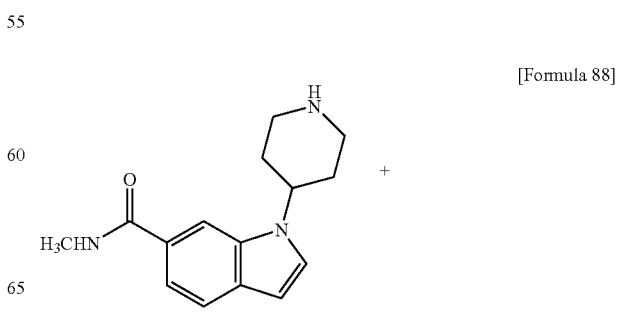

-continued

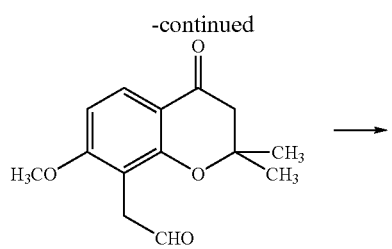

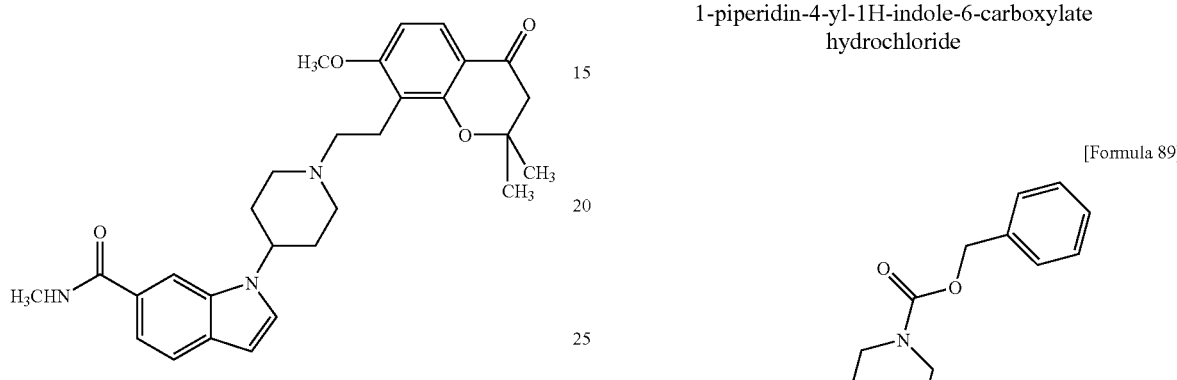

677.7 g (content: 332.8 g, 1.293 mmol) of N-methyl-1-(piperidin-4-yl)-1H-indole-6-carboxamide synthesized in Production Example 7 and 2000 mL of tetrahydrofuran were added to a 15 L four-necked round bottom flask under a nitrogen gas stream. Furthermore, 426.4 g (content: 369.2 g; 1.15 equivalents) of (7-methoxy-2,2-dimethyl-4-oxochroman-8-yl)acetaldehyde obtained in Example 8, 1328 mL of tetrahydrofuran and 148 mL (2.0 molar equivalent) of acetic acid were sequentially added to this suspension, and the reaction mixture was stirred for one hour from a time point when the dissolution of the starting substances was confirmed at room temperature. Subsequently the reaction mixture was cooled to below 10° C. with an ice-water bath and sodium triacetoxyborohydride (356.3 g; 1.3 molar equivalents) was added portionwise divided into four to the reaction mixture. After about 10 minutes, the ice-water bath was changed to a water bath (21.9° C.) and the mixture was stirred under temperature control. The reaction mixture was sampled about 1 hour later and analyzed by HPLC and the end of the reaction was confirmed. The reaction vessel was cooled with an ice-water bath and 4500 mL of ethyl acetate was added to the reaction mixture at about 10° C. Then 5200 mL of 1 N aqueous sodium hydroxide was cast into the reaction mixture for 36 minutes.

The reaction mixture was transferred to a 20 L separatory funnel and rinsed with 2156 mL of ethyl acetate, and the organic layer was separated. The organic layer was sequentially washed with 1000 g of 7% sodium hydrogen carbonate aqueous solution, 5% sodium chloride solution (3328 g, 1000 g, twice) and 3328 mL of water.

The organic layer was concentrated in vacuo, added with 1664 mL of ethanol and concentrated, and 1902.6 g of the obtained solution was subjected to assay. Content of the title compound was 581.1 g, yield was 91.8%, and HPLC purity was 92.5%.

The concentrate was added with 1664 mL of ethanol and dissolved and stirred for about 1 hour after addition of 57.0 g of activated carbon. The activated carbon was removed by filtration through Hyflo Super-Cel and washed with 400 mL of ethanol. The filtrate was concentrated in vacuo (bath temperature: 40° C.) and 1461.8 g of the title compound was obtained as a brown oil.

Content: 552.5 g; HPLC purity: 92.5%

EXAMPLE 11

Synthesis of methyl 1-piperidin-4-yl-1H-indole-6-carboxylate hydrochloride

[Formula 89]

27.5 g of methyl 1-(1-benzyloxycarbonylpiperidin-4-yl)-1H-indole-6-methylcarboxylate was dissolved in 68.75 mL of methanol and 68.75 mL of tetrahydrofuran and stirred for about 7.5 hours in the presence of 1.1 g of 10% palladium on carbon (about 50% water containing product) under 0.3 MPa hydrogen atmosphere. The catalyst was removed by filtration and the solvent was evaporated and 16.69 g of a mixture was obtained. Of these, 6.96 g was used and dissolved in 77 mL of 2-propanol and 2.73 mL of concentrated hydrochloric acid was gradually added while ice cooled. Precipitated crystals were collected by filtration, and the crystals were washed with 2-propanol. After vacuum drying, 5.89 g of the title compound was obtained.

$^1$H-NMR (400 MHz, DMSO-$d_6$) δ (ppm): 2.00-2.30 (m, 4H), 3.05-3.25 (m, 2H), 3.30-3.50 (m, 2H), 3.85 (s, 3H), 4.80-5.00 (m, 1H), 6.61 (d, J=3.1 Hz, 1H), 7.61 (d, J=3.1 Hz, 1H), 7.60-7.70 (m, 2H), 8.26 (s, 1H).

EXAMPLE 12

Synthesis of methyl 1-{1-[2-(7-methoxy-2,2-dimethyl-4-oxochroman-8-yl)ethyl]piperidin-4-yl}-1H-indole-6-carboxylate

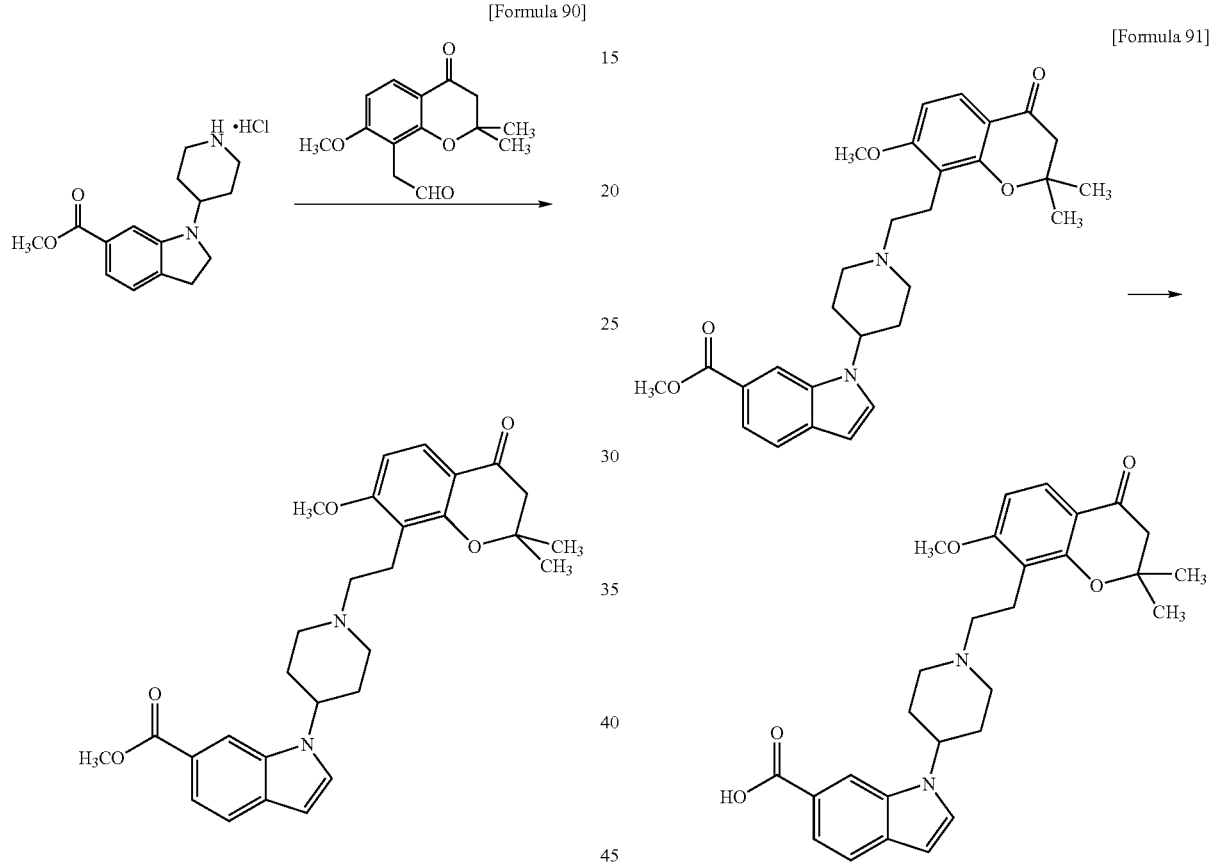

[Formula 90]

2.92 g of methyl 1-piperidin-4-yl-1H-indole-6-carboxylate hydrochloride and 2.92 g of (7-methoxy-2,2-dimethyl-4-oxochroman-8-yl)acetaldehyde were added with 58.4 mL of tetrahydrofuran and 14.6 mL of acetic acid warmed to 40° C. and the reaction mixture was stirred for about 3 hours. The reaction mixture was cooled with an ice-water bath, and 2.52 g of sodium triacetoxyborohydride was added portionwise divided into three. The reaction mixture was warmed to room temperature and 30 minutes later, progress of the reaction was confirmed. The reaction mixture was cooled with an ice-water bath again and 87 mL of toluene and 29 mL of water were added thereto and the aqueous layer was discarded. The organic layer was washed with 49 mL, 69 mL, 30 mL of 1 N aqueous sodium hydroxide sequentially and then with 29 mL, 14 mL of 5% sodium chloride solution and 14 mL of water. The solvent was evaporated and 4.80 g of the crude title compound was obtained.

$^1$H-NMR (400 MHz, CDCl$_3$) δ (ppm): 1.47 (s, 6H), 2.10-2.20 (m, 4H), 2.25-2.40 (m, 2H), 2.50-2.60 (m, 2H), 2.69 (s, 2H), 2.85-2.95 (m, 2H), 3.20-3.35 (m, 2H), 3.90 (s, 3H), 3.96 (s, 3H), 4.30-4.45 (m, 1H), 6.50-6.60 (m, 1H), 6.59 (d, J=8.8 Hz, 1H), 7.42 (d, J=3.1 Hz, 1H), 7.64 (d, J=8.4 Hz, 1H), 7.79 (dd, J=8.40, 1.50 Hz, 1H), 7.80 (d, J=8.8 Hz, 1H), 8.16 (s, 1H).

EXAMPLE 13

Synthesis of 1-{1-[2-(7-methoxy-2,2-dimethyl-4-oxochroman-8-yl) ethyl]piperidin-4-yl}-1H-indole-6-carboxylic acid

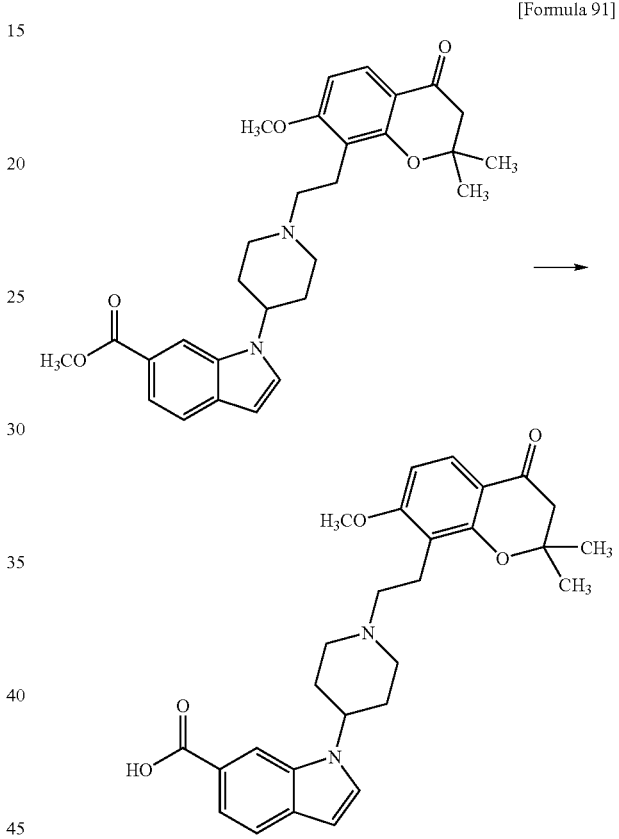

[Formula 91]

3.5 g of the above crude product of methyl 1-{1-[2-(7-methoxy-2,2-dimethyl-4-oxochroman-8-yl)ethyl]piperidin-4-yl}-1H-indole-6-carboxylate was dissolved in 28.0 mL of tetrahydrofuran and added with 14 mL of 1 N aqueous sodium hydroxide. 14 mL of methanol was added and the mixture was heated to 40° C. and stirred for 30 minutes. 7 mL of tetrahydrofuran and 3.5 mL of methanol were added and the mixture was stirred for 2 hours and further stirred at the same temperature for about 16 hours. When the reaction mixture was cooled with an ice-water bath and the pH was adjusted to 7 with 12.2 mL of 1 N hydrochloric acid and 0.5 mL of 1 N sodium hydroxide, crystals precipitated. 10 mL of water was further added to this slurry, and crystals were obtained by filtration and the crystals were washed with 21 mL of a mixture of 2-propanol and water (5:1). The crystals were dried in vacuo and 2.45 g of the title compound was obtained.

$^1$H-NMR (400 MHz, DMSO-d$_6$) δ (ppm): 1.39 (s, 6H), 1.90-2.10 (m, 4H), 2.20-2.35 (m, 2H), 2.40-2.50 (m, 2H), 2.70 (s, 2H), 2.70-2.80 (m, 2H), 3.05-3.15 (m, 2H), 3.85 (s, 3H), 4.40-4.55 (m, 1H), 6.53 (dJ=3.4 Hz, 1H), 6.73 (d, J=8.8

Hz, 1H), 7.57 (d, J=8.0 Hz, 1H), 7.61 (dd, J=8.0, 1.2 Hz, 1H), 7.63 (d, J=8.8 Hz, 1H), 7.72 (d, J=3.4 Hz, 1H), 8.15 (s, 1H).

EXAMPLE 14

Synthesis of methyl 1-{1-[2-(7-methoxy-2,2-dimethyl-4-oxochroman-8-yl)ethyl]piperidin-4-yl}-1H-indole-6-carboxylate

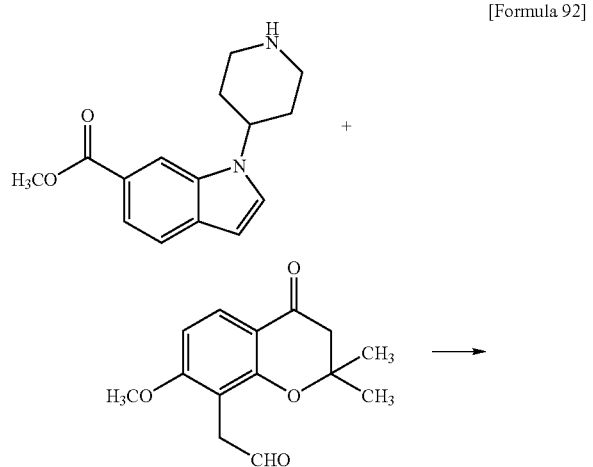

[Formula 92]

28 mL of DME, 14 mL of tetrahydrofuran and 1.24 mL of acetic acid were added to 2.80 g of methyl 1-piperidin-4-yl-1H-indole-6-carboxylate and 3.16 g of (7-methoxy-2,2-dimethyl-4-oxochroman-8-yl)acetaldehyde. Although crystals precipitated, the reaction mixture was stirred for one hour as it was. The reaction mixture was cooled with an ice-water bath, and 2.75 g of sodium triacetoxyborohydride was added portionwise divided into three to the reaction mixture. The reaction mixture was warmed to room temperature and added with 3 mL of tetrahydrofuran and about 1.5 hours later, progress of the reaction was confirmed. The reaction mixture cooled with an ice-water bath again and added with 68 mL of toluene and 29 mL of water and, after clarification and filtration, added with 30 mL of toluene and the aqueous layer was discarded. The organic layer was washed with 29 mL of 1 N aqueous sodium hydroxide, 29 mL×2 of 5% sodium chloride solution and 29 mL of water. The solvent was evaporated and 5.62 g of the crude title compound was obtained.

EXAMPLE 15

Synthesis of 1-{1-[2-(7-methoxy-2,2-dimethyl-4-oxochroman-8-yl)ethyl]piperidin-4-yl}-1H-indole-6-carboxylic acid

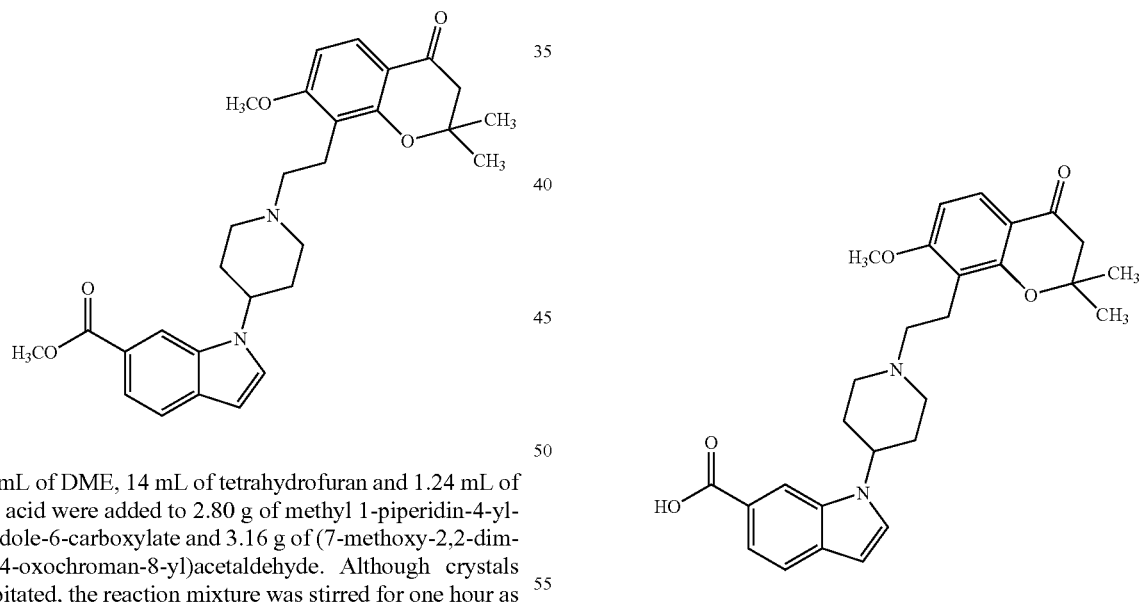

[Formula 93]

4.0 g of the above crude product of methyl 1-{1-[2-(7-methoxy-2,2-dimethyl-4-oxochroman-8-yl)ethyl]piperidin-4-yl}-1H-indole-6-carboxylate was dissolved in 40.0 mL of tetrahydrofuran and added with 16 mL of 1 N aqueous sodium hydroxide. 20 mL of methanol was added to remove the separation of layers of the reaction mixture, and the reaction mixture was stirred at 40° C. for about 20.5 hours. When the reaction mixture was cooled with an ice-water bath and the pH was adjusted to 7 with 15 mL of 1 N hydrochloric acid, crystals precipitated. 10 mL of water was further added to this slurry, and crystals were obtained by filtration and the crystals were washed with 24 mL of a mixture of 2-propanol and water (1:5). The crystals were dried in vacuo and 3.34 g of the title compound was obtained.

EXAMPLE 16

Synthesis of 1-{1-[2-(7-methoxy-2,2-dimethyl-4-oxochroman-8-yl)ethyl]piperidin-4-yl}-N-methyl-1H-indole-6-carboxamide

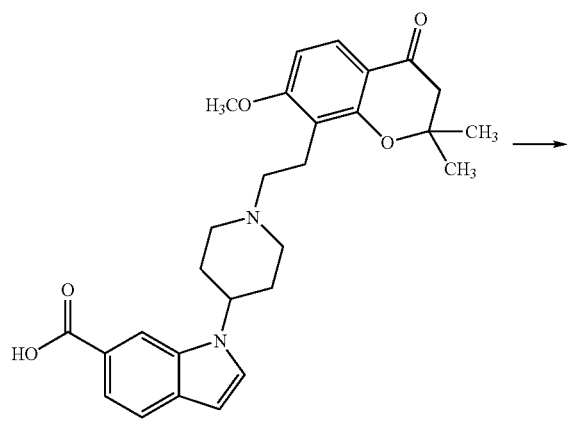
[Formula 94]

1.0 g of 1-{1-[2-(7-methoxy-2,2-dimethyl-4-oxochroman-8-yl)ethyl]piperidin-4-yl}-1H-indole-6-carboxylic acid was dissolved in 25 mL of ethanol, added with 851 mg of 1,1'-cabonyldiimidazole and the reaction mixture was stirred at 40° C. for 2 hours. The reaction mixture was cooled with an ice-water bath, added 1.81 mL of 40% methylamine aqueous solution thereto and stirred for 50 minutes. The reaction mixture was added with 40 mL of ethyl acetate and 20 mL of water and the organic layer was separated. The organic layer was washed with 20 mL of 10% sodium chloride solution and added with 8.5 mL of 1 N hydrochloric acid to adjust the pH to 7. The aqueous layer was discarded and the organic layer was washed with 10 mL of water. The organic layer was concentrated in vacuo, added with 3 mL of 1-propanol and concentrated again and the title compound was obtained.

The compound of Example 6 can be prepared by the following Referential Examples.

REFERENTIAL EXAMPLE 1

Synthesis of 2,6-diacetoxytoluene

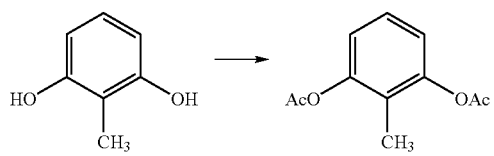
[Formula 95]

15.0 mL of acetic anhydride (16.3 g, 160 mmol) was added dropwise to 62 mL of acetonitrile suspension of 6.2 g (50 mmol) of 2,6-dihydroxytoluene and 27.6 g (200 mmol) of potassium carbonate, which was stirred on an ice-water bath, over 3 minutes. The stirring was stopped 27 minutes later and the reaction mixture was allowed to stand at room temperature overnight and then filtered. The filtrate was stirred and settled in a separatory funnel as 100 mL of toluene and 50 mL of water was added. The aqueous layer was discarded, and the organic layer was washed with 25 mL of water twice, and the solvent was evaporated to obtain 10.3 g of title compound.

$^1$H-NMR (400 MHz, CDCl$_3$) δ (ppm): 2.00 (s, 3H), 2.33 (s, 6H), 6.95 (d, J=8.1 Hz, 2H), 7.24 (t, J=8.3 Hz, 1H)

REFERENTIAL EXAMPLE 2

Synthesis of 2-diacetoxy-6-hydroxytoluene

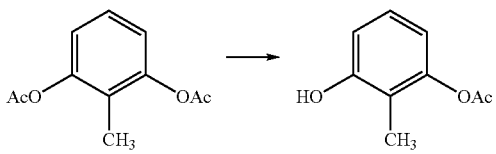
[Formula 96]

8.22 g (39.5 mmol) of 2,6-diacetoxytoluene was dissolved to 82 mL of ethyleneglycol dimethyl ether, added with 14.9 g (395 mmol) of sodium borohydride, heated and stirred on a 60° C. water bath for 9 hours and 44 minutes. The reaction mixture which had been allowed to stand at room temperature overnight was added to a mixture of 100 mL of toluene and 100 mL of water stirred on an ice-water bath, and after stirred for 5 minutes, transferred to a separatory funnel and then settled. The separated aqueous layer was extracted with 50 mL of toluene, and after the combined organic layer was washed with 50 mL of water twice, the solvent was evaporated to obtain 5.01 g of title compound.

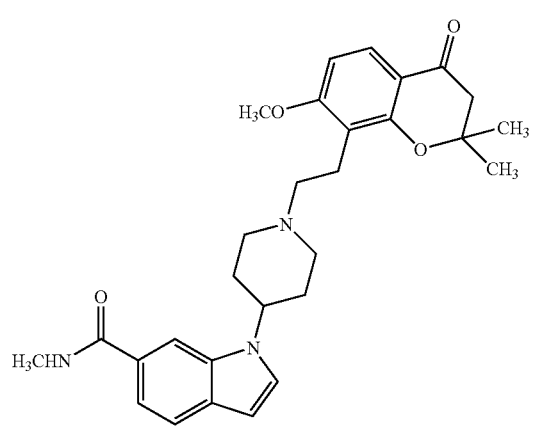

¹H-NMR (400 MHz, CDCl₃) δ (ppm): 2.04 (s, 3H), 2.34 (s, 3H), 6.63 (d, J=8.8 Hz, 1H), 6.65 (d, J=8.3 Hz, 1H), 7.05 (t, J=8.3 Hz, 1H).

REFERENTIAL EXAMPLE 3

Synthesis of 2-acetoxy-6-methoxytoluene

[Formula 97]

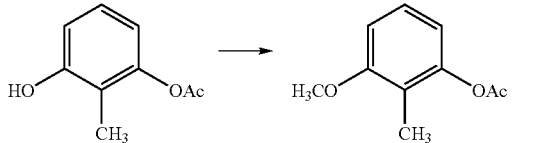

A solution of 5.01 g (30.0 mmol) of 2-acetoxy-6-hydroxytoluene in 50 mL of acetonitrile was added with 12.44 g (90.0 mmol) of potassium carbonate and 12.77 g (90.0 mmol) of methyl iodide and heated and stirred on a 90° C. oil bath for 96 minutes. The reaction mixture which had been allowed to stand at room temperature for about 3 hours was added to a mixture of 100 mL of toluene and 100 mL of water stirred on an ice-water bath, and after stirred for two minutes, transferred to a separatory funnel and then settled. The aqueous layer was separated and discarded and after the organic layer was washed with 20 mL of 1 N aqueous sodium hydroxide and 20 mL of water three times, and the solvent was evaporated to obtain 4.69 g of title compound.

¹H-NMR (400 MHz, CDCl₃) δ (ppm): 2.03 (s, 3H), 2.32 (s, 3H), 3.84 (s, 3H), 6.65 (d, J=8.0 Hz, 1H), 6.74 (d, J=8.1 Hz, 1H), 7.16 (t, J=8.3 Hz, 1H).

REFERENTIAL EXAMPLE 4

Synthesis of 2-hydroxy-6-methoxytoluene

[Formula 98]

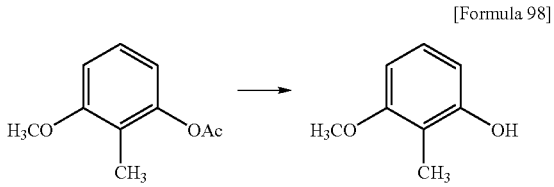

A solution of 18.0 mL of concentrated sulfuric acid in 90 mL water was added to a solution of 4.69 g (26.0 mmol) of 2-acetoxy-6-methoxytoluene in 360 mL ethanol and heated and stirred on a 120° C. oil bath for 36 minutes. The reaction mixture which had been allowed to stand at room temperature overnight was transferred to a separatory funnel, extracted with 50 mL and 20 mL of toluene, and after the combined organic layers were washed with 30 mL of water, 30 mL of 5% sodium hydrogen carbonate aqueous solution and 30 mL of water twice, the solvent was evaporated to obtain 3.15 g of title compound.

¹H-NMR (400 MHz, CDCl₃) δ (ppm): 2.12 (s, 3H), 3.82 (s, 3H), 4.71 (s, 1H), 6.45 (d, J=8.3 Hz, 1H), 6.48 (d, J=8.8 Hz, 1H), 7.03 (t, J=8.3 Hz, 1H).

REFERENTIAL EXAMPLE 5

Synthesis of 2-(N,N-diethylcarbamoyloxy)-6-methoxytoluene

[Formula 99]

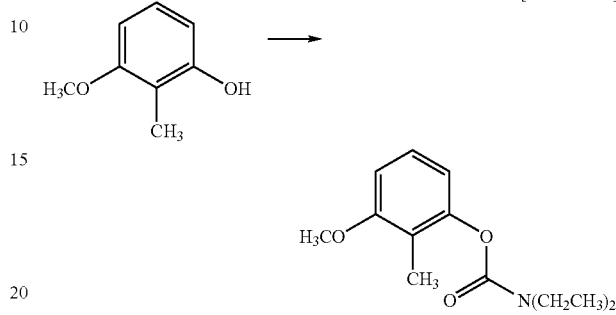

A solution of 3.15 g (22.8 mmol) of 2-hydroxy-6-methoxytoluene in 16 mL acetonitrile was added with 3.50 g (25.1 mmol) of potassium carbonate and 3.4 g (25.1 mmol) of diethylcarbamoyl chloride and heated and stirred on a 100° C. oil bath for 59 minutes. After addition of 0.6 g (4.4 mmol) of diethylcarbamoyl chloride and heated for 38 minutes, while stirring on an ice-water bath, 30 mL of toluene and 30 mL of water, were added into the reaction mixture, and the mixture was stirred for 20 minutes, transferred to a separatory funnel and settled. The aqueous layer was separated and discarded and after the organic layer was washed with 10 mL of 2 N aqueous sodium hydroxide and 10 mL of water twice, and the solvent was evaporated to obtain 5.58 g of the crude title compound. Since the mixture solidified, a part thereof was obtained as seed crystals.

5.58 g of the crude product of the title compound was heated, stirred and dissolved in 14.5 mL of ethanol and 8.9 mL of water on a 50° C. water bath and cooling was allowed to start at room temperature. When the temperature of the solution became 35° C., seed crystals were added therein and after the beginning of crystallization was confirmed it was cooled with a water bath and an ice-water bath. The mixture was stirred on an ice-water bath for about 1 hour and when the crystallizing mixture's temperature was 2.2° C., crystals were obtained by filtration and washed with 8 mL of 50% aqueous ethanol. Crystals were dried in vacuo (30° C., 90 minutes) and 3.89 g of the title compound was obtained.

¹H-NMR (400 MHz, CDCl₃) δ (ppm): 1.24 (m, 6H), 2.05 (s, 3H), 3.43 (m, 4H), 3.85 (s, 3H), 6.71 (d, J=8.3 Hz, 1H), 6.71 (d, J=8.1 Hz, 1H), 7.13 (t, J=8.3 Hz, 1H).

REFERENTIAL EXAMPLE 6

Synthesis of N,N-diethyl-(2-hydroxy-6-methoxyphenyl)acetamide

[Formula 100]

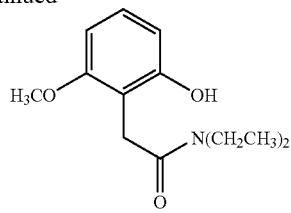

5.0 mL of lithium diisopropylamide (2M/tetrahydrofuran-ethylbenzene, 10 mmol) was stirred and cooled on dry ice-ethanol bath and 8.0 mL tetrahydrofuran solution containing 0.95 g (4.0 mmol) of 2-(N,N-diethylcarbamoyloxy)-6-methoxytoluene was added dropwise thereto over 16 minutes. After one minute, warming was started under room temperature and after the mixture was stirred for 47 minutes, it was allowed to stand overnight. 10 mL of toluene and 10 mL of water were added thereto and after the mixture was stirred for 4 minutes, it was transferred into a separatory funnel and settled. The aqueous layer was separated and collected and combined with aqueous layers extracted from the organic layer with 2 N potassium hydroxide aqueous solution twice (5.0 mL for each time). After this aqueous layer was washed with 10 mL of toluene, 10 mL of toluene was added therein and 20 mL of 2 N hydrochloric acid aqueous solution was added thereto while being stirred and the mixture was transferred into a separatory funnel and settled. The organic layer was separated and collected and combined with the organic layer extracted from the aqueous layer with 5 mL of toluene. This organic layer was washed with 5 mL of water twice and then concentrated in vacuo, and thereby 0.81 g of the title compound was obtained.

$^1$H-NMR (400 MHz, CDCl$_3$) δ (ppm): 1.29 (m, 6H), 3.49 (m, 4H), 3.80 (s, 2H), 3.82 (s, 3H), 6.43 (d, J=8.3 Hz, 1H), 6.64 (d, J=8.3 Hz, 1H), 7.11 (t, J=8.3 Hz, 1H).

REFERENTIAL EXAMPLE 7

Synthesis of 4-methoxy-3H-benzofuran-2-one

[Formula 101]

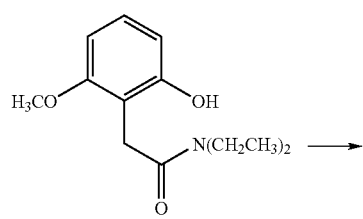

A solution of 0.47 g (2.0 mmol) of N,N-diethyl-(2-hydroxy-6-methoxyphenyl)acetamide in 5.0 mL of toluene was added with 0.92 mL (1.36 g, 12 mmol) of trifluoroacetic acid and heated and stirred on a 125° C. oil bath of for 71 minutes. The mixture was cooled under room temperature, and after that added with 24 mL of 0.5 N aqueous sodium hydroxide, while being stirred, and then transferred into a separatory funnel and settled. The aqueous layer was separated and discarded and after the organic layer was washed with 5 mL of water twice, the solvent was evaporated to obtain 0.27 g of the title compound.

$^1$H-NMR (400 MHz, CDCl$_3$) δ (ppm): 3.66 (s, 2H), 3.86 (s, 3H), 6.67 (d, J=8.3 Hz, 1H), 6.75 (d, J=8.0 Hz, 1H), 7.26 (t, J=8.3 Hz, 1H).

REFERENTIAL EXAMPLE 8

Synthesis of 2-(2-hydroxy-6-methoxyphenyl)ethanol

[Formula 102]

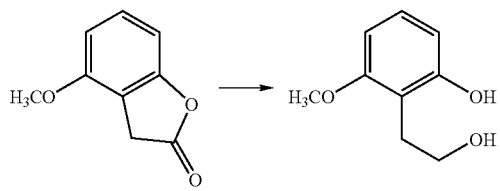

7.18 g (189 mmol) of sodium borohydride was added to a solution of 10.76 g (65.5 mmol) of 4-methoxy-3H-benzofuran-2-one in 150 mL of ethyleneglycol dimethyl ether and stirred. While cooled on an ice-water bath, a solution of 5.25 mL (9.66 g, 94.5 mmol) of concentrated sulfuric acid in 21 mL of ethyleneglycol dimethyl ether was added dropwise thereto over 30 minutes. This mixture was heated and stirred on a 50° C. water bath for 49 minutes and then, while being stirred on an ice-water bath, 32 mL (25.3 g, 790 mmol) of methanol was added dropwise thereto for 6 minutes. This mixture was heated and stirred on a 50° C. water bath for 53 minutes, allowed to stand at room temperature overnight, 300 mL of isopropyl acetate and 200 mL of water were added therein and then the mixture was stirred for 5 minutes, transferred into a separatory funnel and settled. The aqueous layer was separated and discarded and after the organic layer was washed with 100 mL of water twice, the solvent was evaporated. The residue was crystallized from ethyl acetate-hexane and the obtained crystals were dried in vacuo at 30° C. and 3.12 g of the title compound was obtained.

$^1$H-NMR (400 MHz, CDCl$_3$) δ (ppm): 2.98 (t, J=5.1 Hz, 2H), 3.79 (s, 3H), 3.93 (t, J=5.1 Hz, 2H), 6.48 (d, J=8.1 Hz, 1H), 6.59 (d, J=8.0 Hz, 1H), 7.09 (t, J=8.0 Hz, 1H).

REFERENTIAL EXAMPLE 9

Synthesis of 2-(2-hydroxy-6-methoxyphenyl)ethyl acetate

[Formula 103]

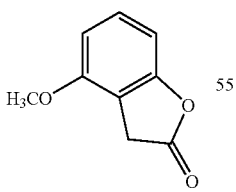

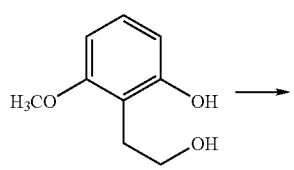

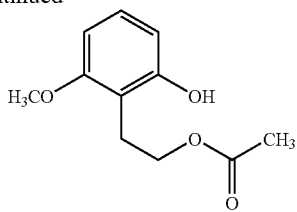

1.0 mL (1.8 g, 18 mmol) of concentrated sulfuric acid was added dropwise to a solution of 0.27 g (1.6 mmol) of 2-(2-hydroxy-6-methoxyphenyl)ethanol in 5.0 mL of acetic acid while being cooled on an ice-water bath. This mixture was stirred under room temperature for 5 minutes and 6.0 mL (4.7 g, 102 mmol) of ethanol was added dropwise thereto. 20 mL of toluene and 20 mL of water were added to this mixture and after stirred for 5 minutes, the mixture was transferred to a separatory funnel and settled. The aqueous layer was separated and discarded and after the organic layer was washed with 100 mL of water twice, the solvent evaporated to obtain 0.16 g of the title compound.

$^1$H-NMR (400 MHz, CDCl$_3$) δ (ppm): 2.09 (s, 3H), 3.02 (t, J=7.1 Hz, 2H), 3.81 (s, 3H), 4.21 (t, J=7.1 Hz, 2H), 6.48 (d, J=8.3 Hz, 1H), 6.53 (d, J=7.8 Hz, 1H), 7.10 (t, J=8.3 Hz, 1H).

REFERENTIAL EXAMPLE 10

Synthesis of 8-(2-acetoxyethyl)-7-methoxy-2,2-dimethylchroman-4-one

[Formula 104]

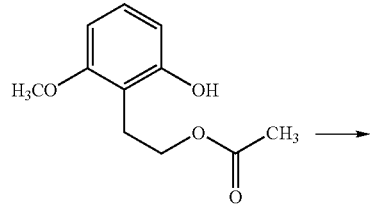

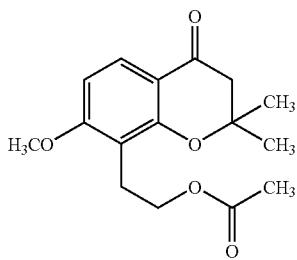

A solution of 5.79 g (27.5 mmol) of 2-(2-hydroxy-6-methoxyphenyl)ethyl acetate, 3.03 g (30.3 mmol) of 2-methylcrotonic acid and 3.26 g (16.9 mmol) of diphosphorus pentaoxide in 29.0 mL of methanesulfonic acid was heated and stirred at 70° C. for 75 minutes. 50 mL of toluene and 50 mL of water were added therein at room temperature and the mixture was stirred for 5 minutes, and then transferred to a separatory funnel and settled. The aqueous layer was separated and discarded and after the organic layer was washed with 25 mL of 5% sodium hydrogen carbonate aqueous solution and 25 mL of water sequentially, the solvent was evaporated to obtain 7.85 g of the crude title compound. This was purified by silica gel chromatography (developing solution composition: 10% ethyl acetate-hexane (volume ratio), Rf: 0.4), and 2.96 g of the title compound was obtained.

$^1$H-NMR (400 MHz, CDCl$_3$) δ (ppm): 1.46 (s, 6H), 2.04 (s, 3H), 2.67 (s, 2H), 2.99 (t, J=7.3 Hz, 2H), 3.88 (s, 3H), 4.18 (t, J=7.3 Hz, 2H), 6.58 (d, J=9.0 Hz, 1H), 7.82 (d, J=8.8 Hz, 1H).

REFERENTIAL EXAMPLE 11

Synthesis of 8-(2-hydroxyethyl)-7-methoxy-2,2-dimethylchroman-4-one

[Formula 105]

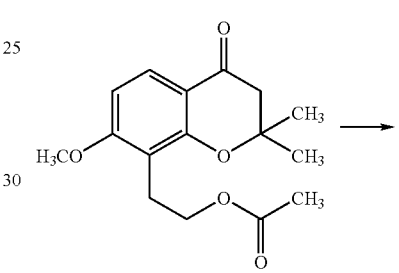

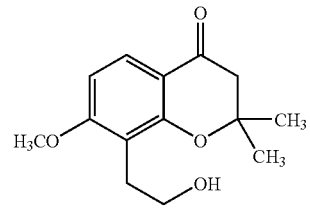

1.80 mL (3.31 g, 32.4 mmol) of concentrated sulfuric acid in 9.0 mL of water was added to a solution of 2.80 g (9.58 mmol) of 8-(2-acetoxyethyl)-7-methoxy-2,2-dimethylchroman-4-one in 18.0 mL of ethanol while being stirred at room temperature and heated and stirred on a 100° C. oil bath for 43 minutes. When the mixture was cooled under room temperature and then 90 mL of toluene and 18 mL of water were added to the mixture, white crystals precipitated and therefore they (crystals 1) were obtained by filtration and crystals (crystals 2) which precipitated when the filtrate was ice cooled were further obtained by filtration. The filtrate obtained here were transferred into a reparatory funnel and settled. The aqueous layer was separated and discarded and after the organic layer was washed with 40 mL of 1 N potassium hydroxide aqueous solution and 20 mL of water twice, the solvent was evaporated, and 2 mL of DME and 5 mL of water were added to the thus obtained concentrate and precipitated crystals (crystal 3) were obtained by filtration. The crystals 1 to 3 were combined and washed with 10 mL of water, and dried in vacuo at 40° C. for one hour to obtain 2.44 g of the title compound.

$^1$H-NMR (400 MHz, CDCl$_3$) δ (ppm): 1.45 (s, 6H), 2.68 (s, 2H), 2.96 (t, J=6.8 Hz, 2H), 3.77 (t, J=6.8 Hz, 2H), 3.89 (s, 3H), 6.59 (d, J=9.0 Hz, 1H), 7.81 (d, J=8.8 Hz, 1H).

INDUSTRIAL APPLICABILITY

The present invention enables to prepare 1-{1-[2-(7-methoxy-2,2-dimethyl-4-oxochroman-8-yl)ethyl]piperidin-4-yl}-N-methyl-1H-indole-6-carboxamide industrially.

The invention claimed is:

1. A production method of 1-{1-[2-(7-methoxy-2,2-dimethyl-4-oxochroman-8-yl)ethyl]piperidin-4-yl}-N-methyl-1H-indole-6-carboxamide represented by the following formula (i):

[Formula 4]

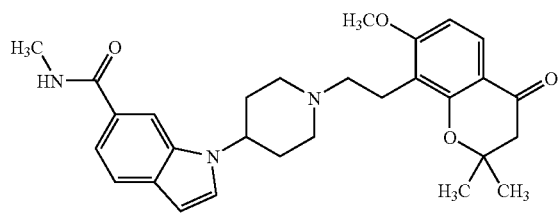

(i)

comprising coupling (7-methoxy-2,2-dimethyl-4-oxochroman-8-yl)acetaldehyde represented by the following formula (a):

[Formula 2]

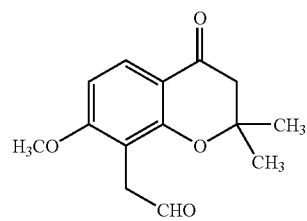

(a)

which is obtained by oxidizing 8-(2-hydroxyethyl)-7-methoxy-2,2-dimethylchroman-4-one represented by the following formula (a-6):

[Formula 1]

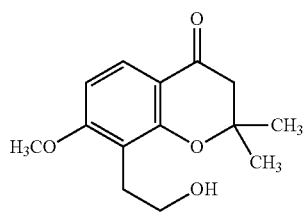

(a-6)

with N-methyl-1-(piperidin-4-yl)-1H-indole-6-carboxamide represented by the following formula (b):

[Formula 3]

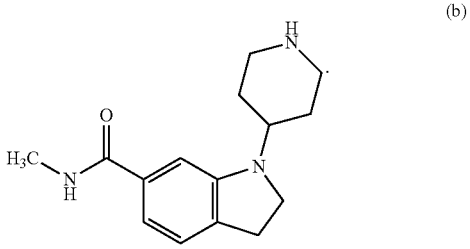

(b)

2. The production method according to claim 1 wherein 8-(2-hydroxyethyl)-7-methoxy-2,2-dimethylchroman-4-one represented by the following formula (a-6):

[Formula 5]

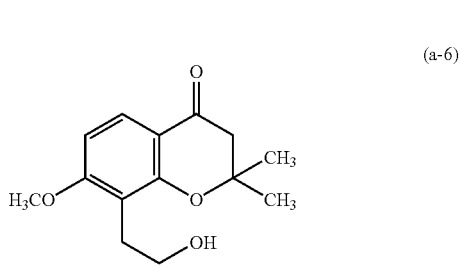

(a-6)

is obtained by removing a protecting group of the compound represented by the following formula (a-5):

[Formula 6]

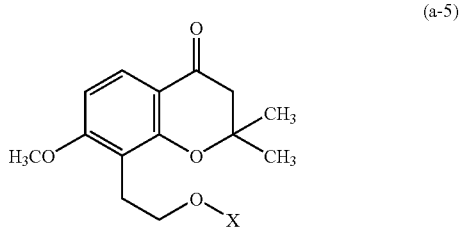

(a-5)

wherein X represents a protecting group of the hydroxyl group.

3. The production method according to claim 1 wherein 8-(2-hydroxyethyl)-7-methoxy-2,2-dimethylchroman-4-one represented by the following formula (a-6):

[Formula 7]

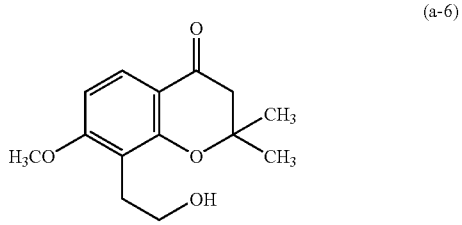

(a-6)

is obtained by reacting the compound represented by the following formula (a-4):

[Formula 8]

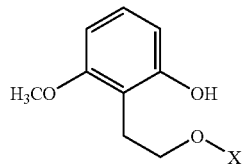
(a-4)

wherein X represents a protecting group of the hydroxyl group, with methylcrotonic acid to obtain a compound represented by the following formula (a-5):

[Formula 9]

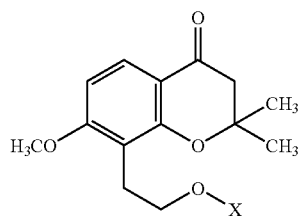
(a-5)

wherein X means the same as defined above, and removing the protecting group of the compound (a-5).

4. The production method according to claim 1 wherein 8-(2-hydroxyethyl)-7-methoxy-2,2-dimethylchroman-4-one represented by the following formula (a-6):

[Formula 10]

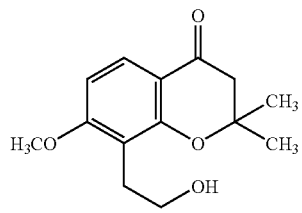
(a-6)

is obtained by reacting the compound represented by the following formula (a-3):

[Formula 11]

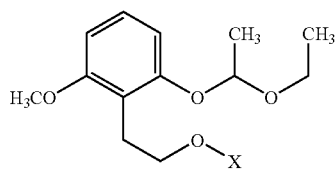
(a-3)

wherein X represents a protecting group of the hydroxyl group, with an acid to obtain a compound represented by the following formula (a-4):

[Formula 12]

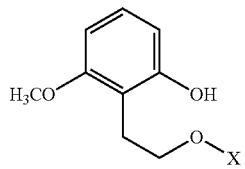
(a-4)

wherein X means the same as defined above, and reacting the compound (a-4) with methylcrotonic acid to obtain a compound represented by the following formula (a-5):

[Formula 13]

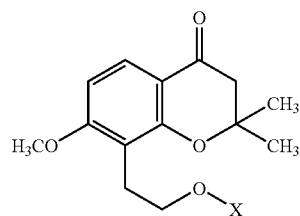
(a-5)

wherein X means the same as defined above, and removing the protecting group of the compound (a-5).

5. The production method according claim 1 wherein 8-(2-hydroxyethyl)-7-methoxy-2,2-dimethylchroman-4-one represented by the following formula (a-6):

[Formula 14]

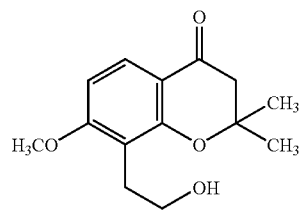
(a-6)

is obtained by protecting a hydroxyl group of 2-[2-(1-ethoxyethoxy)-6-ethoxyphenyl]ethanol represented by the following formula (a-2):

[Formula 15]

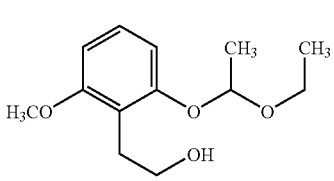
(a-2)

to obtain a compound represented by the following formula (a-3):

[Formula 16]

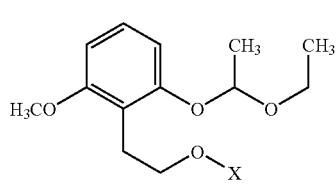
(a-3)

wherein X represents a protecting group of the hydroxyl group, reacting the compound (a-3) with an acid to obtain a compound represented by the following formula (a-4):

[Formula 17]

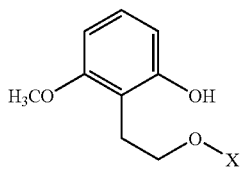
(a-4)

wherein X means the same as defined above, and reacting the compound (a-4) with methylcrotonic acid to obtain a compound represented by the following formula (a-5):

[Formula 18]

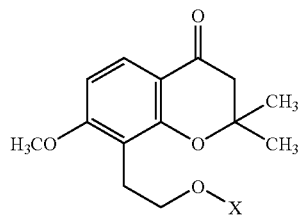
(a-5)

wherein X means the same as defined above, and removing the protecting group of the compound (a-5).

6. The production method according to claim 1 wherein 8-(2-hydroxyethyl)-7-methoxy-2,2-dimethylchroman-4-one represented by the following formula (a-6):

[Formula 19]

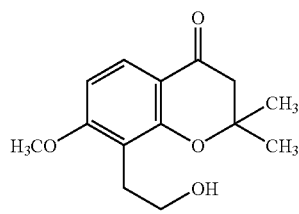
(a-6)

is obtained by reducing ethyl [2-(1-ethoxyethoxy)-6-methoxyphenyl]acetate represented by the following formula (a-1):

[Formula 20]

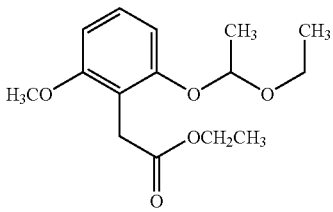
(a-1)

to obtain 2-[2-(1-ethoxyethoxy)-6-methoxyphenyl]ethanol represented by the following formula (a-2):

[Formula 21]

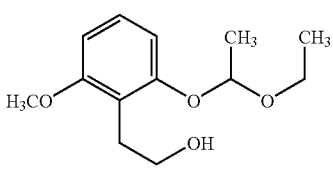
(a-2)

protecting a hydroxyl group of the compound to obtain a compound represented by the following formula (a-3):

[Formula 22]

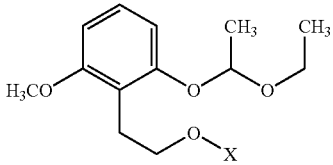
(a-3)

wherein X represents a protecting group of the hydroxyl group, reacting the compound (a-3) with an acid to obtain a compound represented by the following formula (a-4):

[Formula 23]

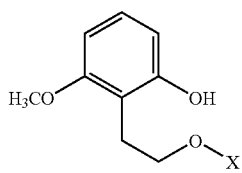
(a-4)

wherein X means the same as defined above, and reacting the compound (a-4) with methylcrotonic acid to obtain a compound represented by the following formula (a-5):

[Formula 24]

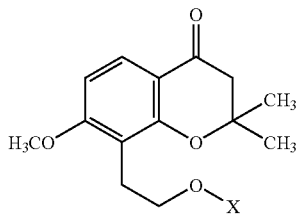
(a-5)

wherein X means the same as defined above, and removing the protecting group of the compound (a-5).

7. The production method according to claim 1 wherein 8-(2-hydroxyethyl)-7-methoxy-2,2-dimethylchroman-4-one represented by the following formula (a-6):

[Formula 25]

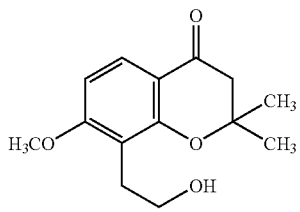
(a-6)

is obtained by reacting 1-(1-ethoxyethoxy)-3-methoxybenzene represented by the following formula:

[Formula 26]

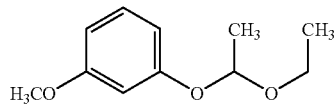

with ethyl bromoacetate to obtain ethyl [2-(1-ethoxyethoxy)-6-methoxyphenyl]acetate represented by the following formula (a-1):

[Formula 27]

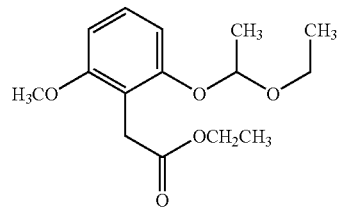
(a-1)

and reducing the compound (a-1) to obtain 2-[2-(1-ethoxyethoxy)-6-methoxyphenyl]ethanol represented by the following formula (a-2):

[Formula 28]

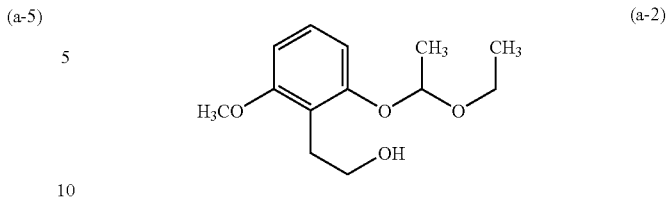
(a-2)

protecting a hydroxyl group of the compound (a-2) to obtain a compound represented by the following formula (a-3):

[Formula 29]

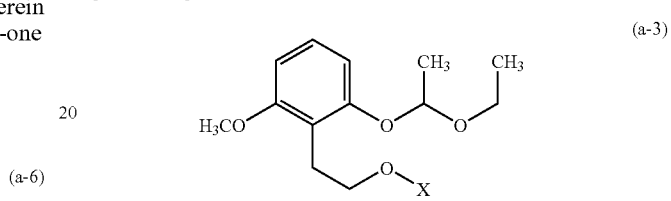
(a-3)

wherein X represents a protecting group of the hydroxyl group, reacting the compound (a-3) with an acid to obtain a compound represented by the following formula (a-4):

[Formula 30]

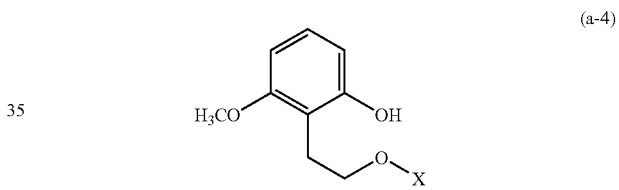
(a-4)

wherein X means the same as defined above, and reacting the compound (a-4) with methylcrotonic acid to obtain a compound represented by the following formula (a-5):

[Formula 31]

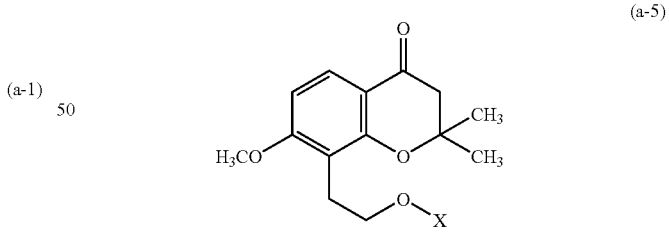
(a-5)

wherein X means the same as defined above, and removing the protecting group of the compound (a-5).

8. The production method according to claim 2 wherein X is a benzoyl group.

* * * * *

UNITED STATES PATENT AND TRADEMARK OFFICE
CERTIFICATE OF CORRECTION

PATENT NO.        : 8,110,688 B2                        Page 1 of 1
APPLICATION NO.   : 11/914115
DATED             : February 7, 2012
INVENTOR(S)       : Naoyuki Shimomura et al.

It is certified that error appears in the above-identified patent and that said Letters Patent is hereby corrected as shown below:

ON THE TITLE PAGE:

At item (22), PCT Filed, change "Nov. 5, 2006" to --May 11, 2006--.

Insert the following as new item (60), Related U.S. Application Data:

--Related U.S. Application Data

(60) U.S. Application No. 11/126,209, filed on May 11, 2005, now abandoned.--

IN THE SPECIFICATION:

Column 1, line 6, change: "claims priority under 119(e) on U.S. Provisional Application" to --claims priority under 120 on U.S. Non-provisional Application--.

Signed and Sealed this
Twenty-sixth Day of June, 2012

David J. Kappos
*Director of the United States Patent and Trademark Office*